(12) United States Patent
Kamio et al.

(10) Patent No.: US 10,929,959 B2
(45) Date of Patent: Feb. 23, 2021

(54) IMAGE PROCESSING APPARATUS, IMAGING APPARATUS, AND IMAGE PROCESSING METHOD

(71) Applicant: SONY CORPORATION, Tokyo (JP)

(72) Inventors: Kazunori Kamio, Kanagawa (JP); Yiwen Zhu, Kanagawa (JP); Takuro Kawai, Tokyo (JP); Takahiro Nagano, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 65 days.

(21) Appl. No.: 16/088,586

(22) PCT Filed: Jan. 25, 2017

(86) PCT No.: PCT/JP2017/002583
§ 371 (c)(1),
(2) Date: Sep. 26, 2018

(87) PCT Pub. No.: WO2017/175452
PCT Pub. Date: Oct. 12, 2017

(65) Prior Publication Data
US 2019/0122345 A1 Apr. 25, 2019

(30) Foreign Application Priority Data
Apr. 4, 2016 (JP) ............... JP2016-075012

(51) Int. Cl.
*G06T 5/00* (2006.01)
*G06T 5/50* (2006.01)
(Continued)

(52) U.S. Cl.
CPC ............ *G06T 5/003* (2013.01); *A61B 1/00* (2013.01); *A61B 1/00009* (2013.01); *A61B 1/04* (2013.01);
(Continued)

(58) Field of Classification Search
CPC . G06T 5/003; G06T 5/50; G06T 2207/30101; G06T 2207/10068;
(Continued)

(56) References Cited

U.S. PATENT DOCUMENTS 7,451,173 B1 * 11/2008 Van Benthem ......... G06F 17/11
708/607
2009/0147999 A1 6/2009 Maeda et al.
(Continued)

FOREIGN PATENT DOCUMENTS

EP 2070469 A1 6/2009
JP 2009-160386 A 7/2009
(Continued)

OTHER PUBLICATIONS

Michael R. Keenan, Jerilyn A. Timlin, Mark H. Van Benthem, and David M. Haaland "Algorithms for constrained linear unmixing with application to the hyperspectral analysis of fluorophore mixtures", Proc. SPIE 4816, Imaging Spectrometry VIII, (Nov. 8, 2002). (Year: 2002).*

(Continued)

*Primary Examiner* — Brenda C Bernardi
(74) *Attorney, Agent, or Firm* — Chip Law Group

(57) ABSTRACT

Provided are an apparatus and a method for executing image quality enhancement processing on a fluorescence image. A fluorescence image and a visible light image are input and the image feature amount is extracted, so as to execute pixel value correction processing on the fluorescence image on the basis of a correction parameter determined in accordance with the feature amount. The correction parameter used for pixel value correction is determined by the correction parameter calculation unit on the basis of the feature amount. The image correction unit executes pixel value correction processing that applies the correction parameter (Continued)

determined by the correction parameter calculation unit. For example, blur mode information is obtained as a feature amount from a fluorescence image, and the image correction unit executes pixel value correction processing on the fluorescence image so as to reduce blur of the fluorescence image.

13 Claims, 19 Drawing Sheets

(51) Int. Cl.
    *A61B 1/00*         (2006.01)
    *A61B 1/04*         (2006.01)
    *A61B 5/00*         (2006.01)
    *G16H 30/00*       (2018.01)
    *G06K 9/46*         (2006.01)

(52) U.S. Cl.
    CPC ............ *A61B 1/043* (2013.01); *A61B 5/0035* (2013.01); *A61B 5/0071* (2013.01); *A61B 5/0084* (2013.01); *A61B 5/7264* (2013.01); *G06K 9/4661* (2013.01); *G06T 5/50* (2013.01); *G16H 30/00* (2018.01); *A61B 2576/00* (2013.01); *G06T 2207/10064* (2013.01); *G06T 2207/10068* (2013.01); *G06T 2207/20201* (2013.01); *G06T 2207/20224* (2013.01)

(58) Field of Classification Search
    CPC . G06T 2207/20224; G06T 2207/20201; G06T 2207/10064; A61B 5/0035; A61B 5/7264; A61B 1/04; A61B 5/0084; A61B 1/043; A61B 1/00; A61B 1/00009; A61B 5/0071; A61B 2576/00; G06K 9/2018; G06K 9/4661; G06K 9/6267; G06K 9/036; G06K 2209/05; G16H 30/00; G16H 30/40

See application file for complete search history.

(56) References Cited

U.S. PATENT DOCUMENTS

| | | | |
|---|---|---|---|
| 2012/0323072 A1* | 12/2012 | Ishihara | A61B 1/00009 600/109 |
| 2013/0150728 A1* | 6/2013 | Takei | A61B 6/52 600/476 |
| 2015/0276602 A1* | 10/2015 | Ishihara | A61B 1/0638 250/458.1 |
| 2015/0305604 A1* | 10/2015 | Melsky | A61B 18/20 600/104 |
| 2016/0007856 A1* | 1/2016 | Ishihara | G02B 23/2469 600/476 |
| 2016/0262622 A1 | 9/2016 | Ishihara | |

FOREIGN PATENT DOCUMENTS

| | | |
|---|---|---|
| JP | 2010-082141 A | 4/2010 |
| JP | 2010-158414 A | 7/2010 |
| JP | 2011-200330 A | 10/2011 |
| JP | 2013-248319 A | 12/2013 |
| WO | 2015/080215 A1 | 6/2015 |

OTHER PUBLICATIONS

International Search Report and Written Opinion of PCT Application No. PCT/JP2017/002583, dated Apr. 11, 2017, 09 pages of ISRWO.

* cited by examiner

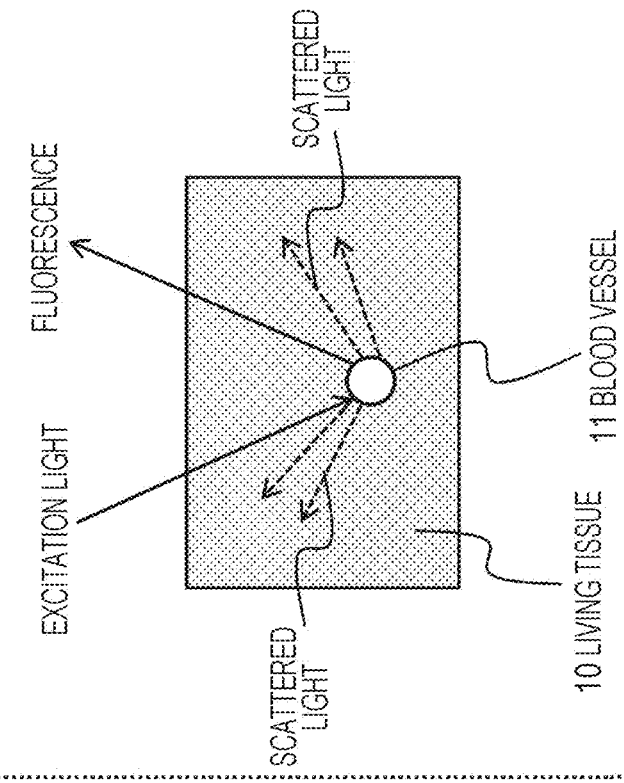
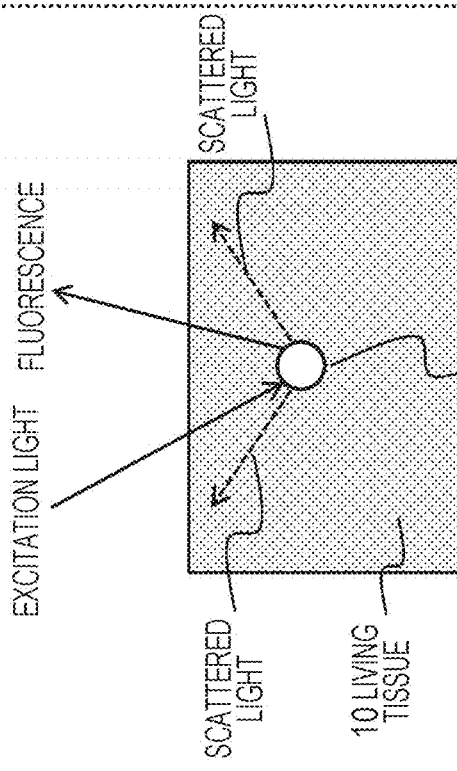

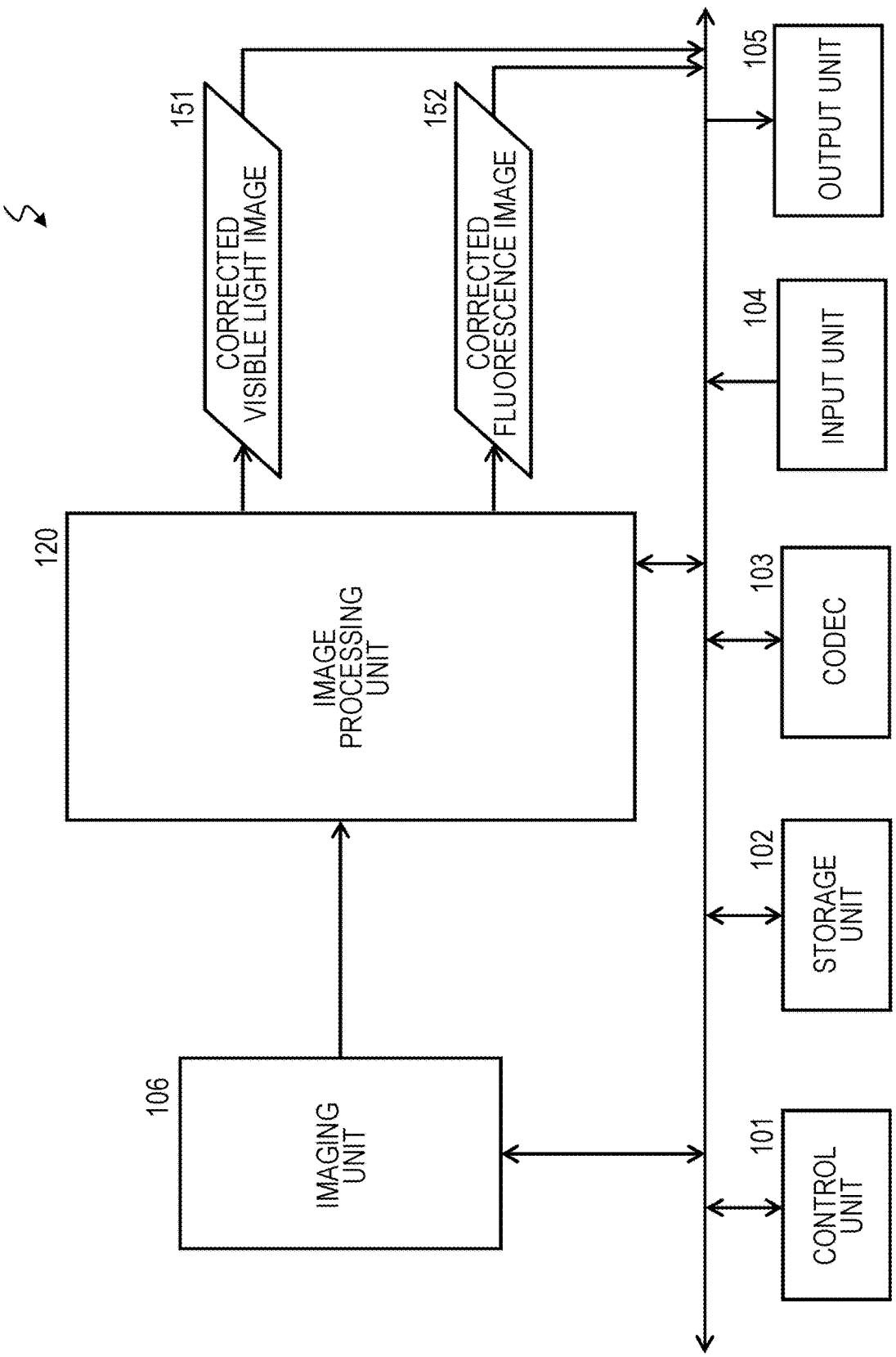

| | FEATURE AMOUNT | SPECIFIC EXAMPLE |
|---|---|---|
| FIG. 4A | POINT SPREAD FUNCTION (PSF: Point Spread Function) INFORMATION (FUNCTION INDICATING BLUR AMOUNT) | |
| FIG. 4B | LUMINANCE DISTRIBUTION INFORMATION | |
| FIG. 4C | NOISE INFORMATION | |

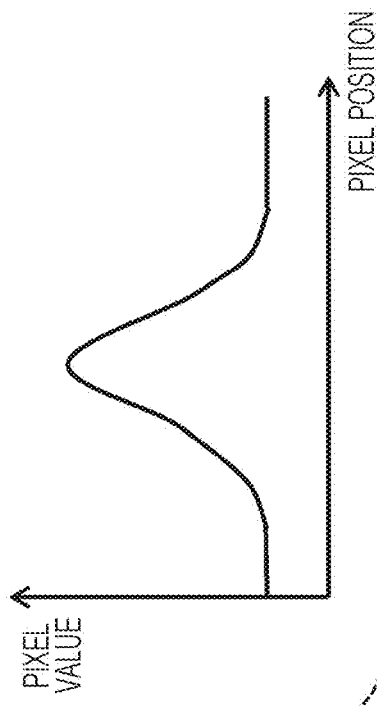
FIG. 8A EXAMPLE OF PIXEL VALUE DISTRIBUTION ON IMAGE BEFORE CORRECTION (EXPANSION OF BLUR = SMALL)
FIG. 8B EXAMPLE OF TAP SETTING AND INVERSE FILTER CONFIGURATION PARAMETER (MULTIPLICATION COEFFICIENT Ki)
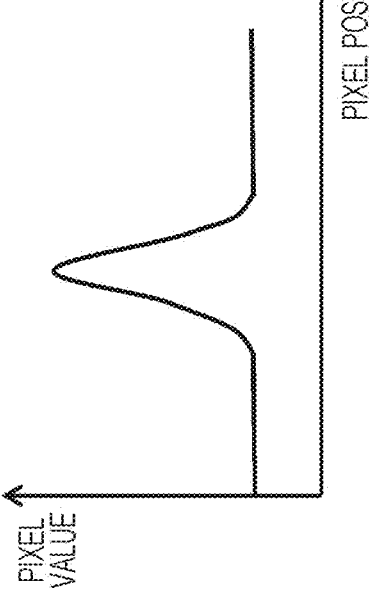
FIG. 8C EXAMPLE OF PIXEL VALUE DISTRIBUTION ON IMAGE AFTER CORRECTION

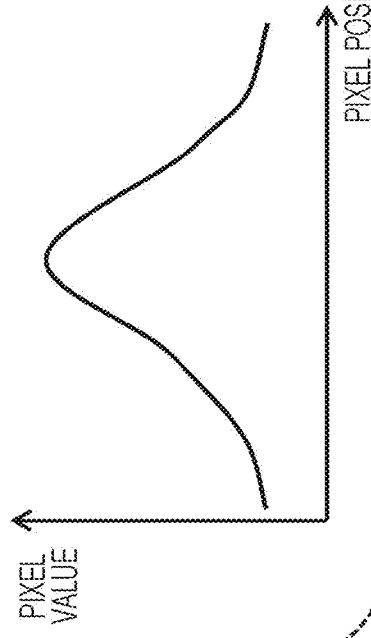
FIG. 9A EXAMPLE OF PIXEL VALUE DISTRIBUTION ON IMAGE BEFORE CORRECTION (EXPANSION OF BLUR = LARGE)
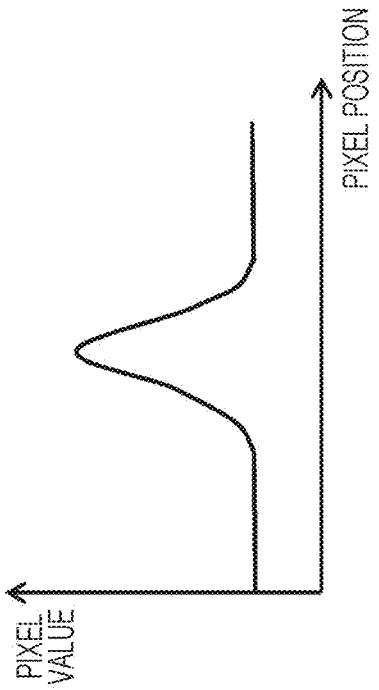
FIG. 9B EXAMPLE OF TAP SETTING AND INVERSE FILTER CONFIGURATION PARAMETER (MULTIPLICATION COEFFICIENT Ki)
FIG. 9C EXAMPLE OF PIXEL VALUE DISTRIBUTION ON IMAGE AFTER CORRECTION

IMAGE PROCESSING APPARATUS, IMAGING APPARATUS, AND IMAGE PROCESSING METHOD

CROSS REFERENCE TO RELATED APPLICATIONS

This application is a U.S. National Phase of International Patent Application No. PCT/JP2017/002583 filed on Jan. 25, 2017, which claims priority benefit of Japanese Patent Application No. JP 2016-075012 filed in the Japan Patent Office on Apr. 4, 2016. Each of the above-referenced applications is hereby incorporated herein by reference in its entirety.

TECHNICAL FIELD

The present disclosure relates to an image processing apparatus, an imaging apparatus, an image processing method, and a program. The present disclosure relates more particularly to an image processing apparatus, an imaging apparatus, an image processing method, and a program for performing image processing using a visible image and a fluorescence image.

BACKGROUND ART

While visible light images being ordinary color images are used for an endoscope that photographs images of the inside of a living body, the use of fluorescence images different from visible light images has advanced recently.

The fluorescence image is an image, for example, obtained by emitting excitation light of a specific wavelength region and then photographing fluorescence contained in reflected light from a substance in the living body.

The fluorescence images can indicate, for example, an intensity difference corresponding to each of lesions in the living body. With the use of fluorescence images, it is possible to effectively perform disease progress status analysis, or the like.

Note that examples of endoscope apparatuses using a visible light image and a fluorescence image are described in documents such as Patent Document 1 (Japanese Patent Application Laid-Open No. 2010-82141), Patent Document 2 (Japanese Patent Application Laid-Open No. 2011-200330), and Patent Document 3 (Japanese Patent Application Laid-Open No. 2013-248319).

The fluorescence image, however, has a disadvantage of having image blur severer than in the case of ordinary visible light images. Particularly, an image of a blood vessel or the like located at a deep position in a living body has a problem that is likely to be unclear due to generation of a great amount of scattered light rays within the living body.

CITATION LIST

Patent Document

Patent Document 1: Japanese Patent Application Laid-Open No. 2010-82141

Patent Document 2: Japanese Patent Application Laid-Open No. 2011-200330

Patent Document 3: Japanese Patent Application Laid-Open No. 2013-248319

SUMMARY OF THE INVENTION

Problems to be Solved by the Invention

The present disclosure is, for example, made in view of the above problems, and aims to provide an image processing apparatus, an imaging apparatus, an image processing method, and a program capable of obtaining a fluorescence image with little blur, for example.

Solutions to Problems

A first aspect of the present disclosure is an image processing apparatus including:
a feature amount classification processing unit that inputs a fluorescence image and a visible light image and extracts a feature amount from at least one of the images; and
an image correction unit that executes pixel value correction processing on the fluorescence image on the basis of a correction parameter determined in accordance with the feature amount.

Moreover, a second aspect of the present disclosure is an imaging apparatus including:
an imaging unit that performs imaging processing of a visible light image and a fluorescence image, or a visible-fluorescence mixture image;
an image separating unit that inputs a photographed image of the imaging unit, separates a visible light image and a fluorescence image from the input image and outputs the separated images;
a feature amount classification processing unit that inputs the fluorescence image and the visible light image output by the image separating unit and extracts a feature amount from at least one of the images; and
an image correction unit that executes pixel value correction processing on the fluorescence image output by the image separating unit on the basis of a correction parameter determined in accordance with the feature amount.

Moreover, a third aspect of the present disclosure is an image processing method executed in an image processing apparatus, the image processing method including executing:
a feature amount calculation step of executing, by a feature amount classification processing unit, input of a fluorescence image and a visible light image and extraction of a feature amount from at least one of the images; and
an image correction step of executing, by an image correction unit, pixel value correction processing on the fluorescence image on the basis of a correction parameter determined in accordance with the feature amount.

Moreover, a fourth aspect of the present disclosure is a program that causes an image processing apparatus to execute image processing, the image processing including processing of:
causing a feature amount classification processing unit to input a fluorescence image and a visible light image and extract a feature amount from at least one of the images; and
causing an image correction unit to execute pixel value correction processing on the fluorescence image on the basis of a correction parameter determined in accordance with the feature amount.

Note that the program of the present disclosure is a program that can be provided by a storage medium or a communication medium provided in a computer readable format to an information processing apparatus or a computer system that can execute various program codes, for example. By providing such a program in a computer readable format, processing according to the program is implemented on the information processing apparatus or the computer system.

Still other objects, features and advantages of the present disclosure will be apparent from a detailed description based on exemplary embodiments of the present disclosure to be described below and attached drawings. Note that in the present description, the system represents a logical set of a plurality of apparatuses, and that all the constituent apparatuses need not be in a same housing.

Effects of the Invention

According to a configuration of one exemplary embodiment of the present disclosure, it is possible to implement an apparatus and a method to execute image quality enhancement processing on fluorescence images.

Specifically, the fluorescence image and the visible light image are input and the image feature amount is extracted, and pixel value correction processing is executed on the fluorescence image on the basis of a correction parameter determined in accordance with the feature amount. The correction parameter used for pixel value correction is determined by a correction parameter calculation unit on the basis of the feature amount. The image correction unit executes pixel value correction processing that applies the correction parameter determined by the correction parameter calculation unit. For example, blur mode information is obtained as a feature amount from a fluorescence image, and the image correction unit executes pixel value correction processing on the fluorescence image so as to reduce blur of the fluorescence image.

This processing enables implementation of an apparatus and a method for executing image quality enhancement processing on a fluorescence image.

Note that effects described in the present description are provided for purposes of exemplary illustration and are not intended to be limiting. Other additional effects may also be contemplated.

BRIEF DESCRIPTION OF DRAWINGS

FIGS. 1A and 1B are diagrams illustrating fluorescence images.

FIG. 2 is a diagram illustrating a configuration example of an image processing apparatus.

FIGS. 4A1, 4A2, 4B1, 4B2, 4C1, and 4C2 are diagrams illustrating an image feature amount.

FIGS. 8A, 8B, and 8C are diagrams illustrating a processing example executed by an image processing unit.

FIGS. 9A, 9B, and 9C are diagrams illustrating a processing example executed by an image processsing unit.

MODE FOR CARRYING OUT THE INVENTION

Figure 3:
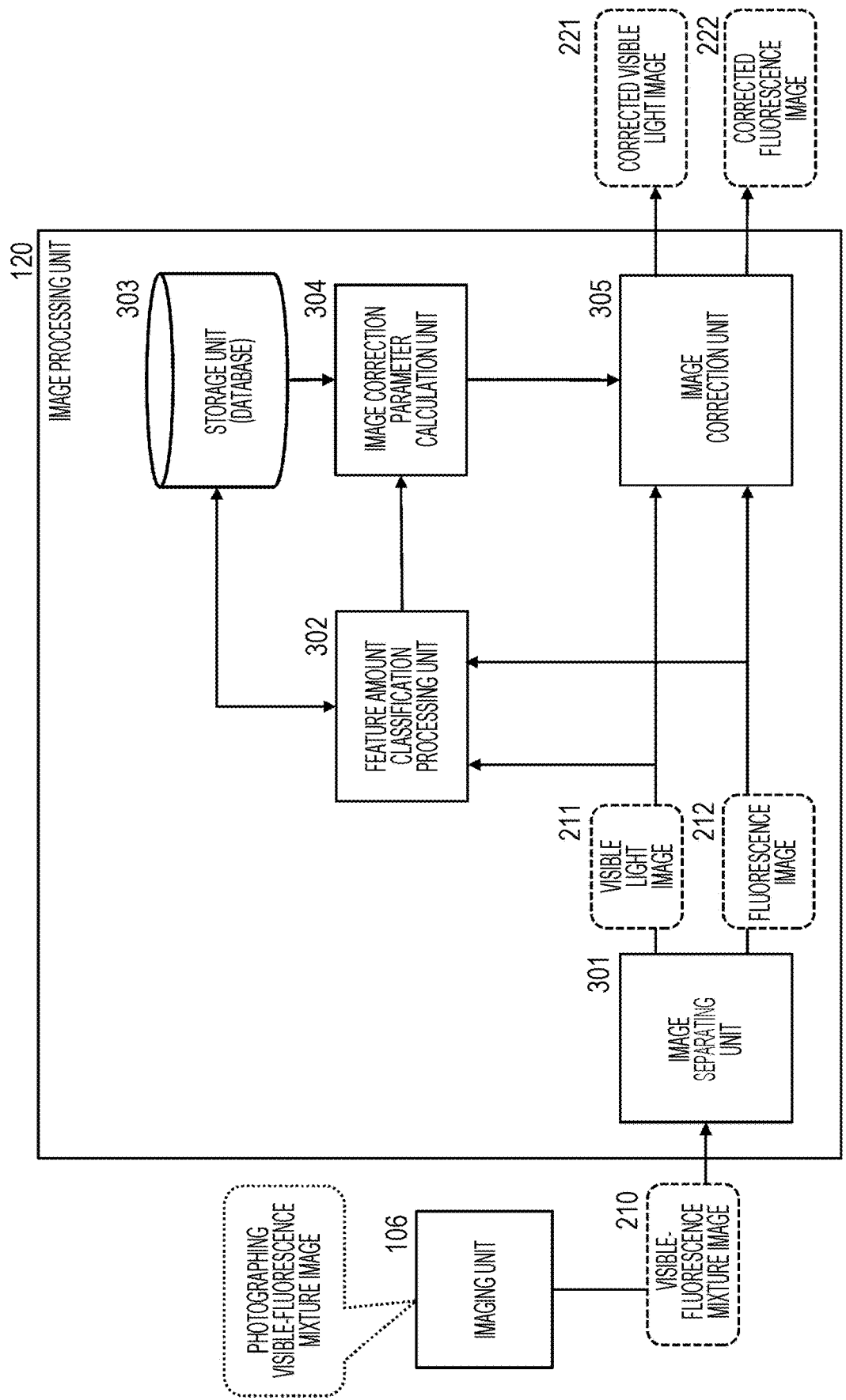
FIG. 3 is a diagram illustrating configuration and processing of an image processing unit.

Hereinafter, details of an image processing apparatus, an imaging apparatus, an image processing method, and a program of the present disclosure will be described with reference to the drawings. Note that the description will be given in the order of following items.

1. Outline of fluorescence image
2. Configuration and processing of image processing apparatus of the present disclosure
3. Configuration for executing image quality enhancement processing applying blur mode information (PSF information) as image feature amount
4. Configuration for executing image interpolation processing and applying interpolation image to execute image correction as image quality enhancement processing
5. Example of correction processing mode of fluorescence image according to image photographing sequence
6. Processing sequence executed by image processing apparatus
  6-1. Basic sequence of image processing
  6-2. Image processing sequence in a configuration executing time sharing photographing of visible light image and fluorescence image
  6-3. Image processing sequence in a configuration of consecutively photographing images according to mode by setting image photographing modes of visible light images and fluorescence images
7. Hardware configuration example of image processing apparatus
8. Summary of configuration of present disclosure

[1. Outline of Fluorescence Image]

First, an outline of a fluorescence image will be described.

As described above, while visible light images being ordinary color images are used for an endoscope that photographs images of the inside of a living body, the use of fluorescence images different from visible light images has been increasing recently.

A fluorescence image is an image obtained by emitting excitation light of a specific wavelength and then photographing fluorescence contained in reflected light from a substance in the living body.

The fluorescence images can indicate, for example, an intensity difference corresponding to each of lesions in the living body. With the use of fluorescence images, it is possible to effectively perform disease progress status analysis, or the like.

A configuration of photographing a fluorescence image will be described with reference to FIGS. 1A and 1B.

A fluorescence image is an image obtained by photographing by emitting excitation light of a specific wavelength and then inputting fluorescence output from a living tissue such as blood vessel to an imaging element, for example.

FIG. 1A illustrates a configuration example of photographing a blood vessel 11 located in a relatively shallow portion in a living tissue 10, and FIG. 2B illustrates a configuration example of photographing a blood vessel 11 located in a relatively deep portion in the living tissue 10.

When the excitation light is emitted onto the blood vessel, a plurality of scattered light rays is generated. In particular, more scattered light rays are generated in a deep portion of the living tissue 10, and this leads to a problem of increasing blur in the fluorescence image photographed by the imaging element.

The image processing apparatus according to the present disclosure reduces blur in a fluorescence image for example, making it possible to generate a fluorescence image with less blur.

Hereinafter, configuration and processing of the image processing apparatus according to the present disclosure will be described in detail.

[2. Configuration and Processing of Image Processing Apparatus of Present Disclosure]

Configuration and processing of the image processing apparatus of the present disclosure will be described with reference to FIG. 2 and the subsequent figures.

FIG. 2 is a block diagram illustrating a configuration of an imaging apparatus, as an example of an image processing apparatus 100 according to the present disclosure.

Note that the image processing apparatus of the present disclosure is not limited to the imaging apparatus, and includes an information processing apparatus such as a PC that inputs a photographed image of the imaging apparatus and executes image processing, for example.

Hereinafter, configuration and processing of the imaging apparatus will be described using an example of the image processing apparatus 100 according to the present disclosure.

Image processing other than the photographing processing described in the following exemplary embodiments is not limited to the imaging apparatus, and can be executed in an information processing apparatus such as a PC.

The image processing apparatus 100 as an imaging apparatus illustrated in FIG. 2 includes a control unit 101, a storage unit 102, a codec 103, an input unit 104, an output unit 105, an imaging unit 106, and an image processing unit 120.

The imaging unit 106 photographs a visible-fluorescence mixture image including both photographing light in a visible light region constituting an ordinary color image, and photographing light in a fluorescent region.

Alternatively, a visible light image being an ordinary color image and a fluorescence image are photographed separately. For example, the two types of images are photographed alternately.

As described above, a fluorescence image is an image obtained by photographing a fluorescent component contained in reflected light from a substance in the living body.

The control unit 101 controls various types of processing to be executed in the imaging apparatus 100, such as image photographing, signal processing on a photographed image, image recording processing, and display processing. The control unit 101 includes, for example, a CPU that executes processing according to various processing programs stored in the storage unit 102 and functions as a data processing unit that executes programs.

The storage unit 102 is constituted with a storage unit of photographed images, a storage unit for processing program executed by the control unit 101 and various parameters, a RAM, a ROM, or the like, functioning as working areas at the time of data processing.

The codec 103 executes encoding and decoding processing such as compression and decompression processing of photographed images.

The input unit 104 is a user operation unit, for example, and inputs control information such as start and end of photographing, and various mode settings.

The output unit 105 is constituted with a display unit, a speaker, or the like, and is used for display of a photographed image, a through-the-lens image, or the like, and audio output, or the like.

The image processing unit 120 inputs a photographed image from the imaging unit 106 and executes the image quality enhancement processing on the input image.

Specifically, for example, a corrected visible light image 151 with enhanced image quality and a corrected fluorescence image 152 are generated.

Configuration and processing of the image processing unit 120 will be described with reference to FIG. 3 and the subsequent figures.

As illustrated in FIG. 3, the imaging unit 106 according to the present exemplary embodiment photographs a visible-fluorescence mixture image 210 including both photographing light in a visible light region constituting an ordinary color image, and photographing light in a fluorescent region. The visible-fluorescence mixture image 210 photographed by the imaging unit 106 is input to the image processing unit 120.

The image processing unit 120 inputs the visible-fluorescence mixture image 210, generates and outputs a corrected visible light image 221 and a corrected fluorescence image 222 that have undergone image quality enhancement processing.

Processing executed by the image processing unit 120 will be described.

The image processing unit 120 first inputs the visible-fluorescence mixture image 210 photographed by the imaging unit 106 to an image separating unit 301, and then, separates the visible-fluorescence mixture image 210 into a visible light image 211 constituted with a visible light component similar to an ordinary RGB color image, and a fluorescence image 212 constituted with a fluorescent component alone.

This is executed by matrix operation applying separation matrix, for example.

The visible light image 211 and the fluorescence image 212 generated by image separation processing in the image separating unit 301 are input to the feature amount classification processing unit 302 and the image correction unit 305.

The feature amount classification processing unit 302 inputs the visible light image 211 and the fluorescence image 212, extracts an image feature amount from these images, executes classification processing based on the extracted feature amount and stores data into a storage unit (database), while inputting a feature amount data classification result to the image correction parameter calculation unit 304.

Note that classification processing is classification processing in general machine learning.

Herein the classification represents classification for determining the correction mode and the correction parameter as to what types of image correction is effective for image quality enhancement processing on the basis of the feature amount obtained from the image.

Note that training data to be applied to this classification is stored in a storage unit (database) 303, and the feature amount classification processing unit 302 uses the training data stored in the storage unit (database) 303 and determines an optimum correction mode or the like for the image quality enhancement processing for the input image (the visible light image 211, the fluorescence image 212).

The determination information of the correction mode is input to the image correction parameter calculation unit 304.

The image correction parameter calculation unit 304 uses the correction mode determination information input from the feature amount classification processing unit 302 and training data stored in the storage unit (database) 303 to determine the image correction parameter to be used for performing image quality enhancement processing on the visible light image 211 and the fluorescence image 212.

The determined image correction parameter is input to the image correction unit 305.

The image correction unit 305 applies the image correction parameter input from the image correction parameter calculation unit 304 and executes image correction processing on the visible light image 211 and the fluorescence image 212 and then, generates and outputs the corrected visible light image 221 and the corrected fluorescence image 222 that have undergone image quality enhancement processing.

An example of feature amount data obtained by the feature amount classification processing unit 302 from the visible light image 211 and the fluorescence image 212 will be described with reference to FIGS. 4A1, 4A2, 4B1, 4B2, 4C1, and 4C2.

FIGS. 4A1, 4A2, 4B1, 4B2, 4C1, and 4C2 illustrate an example of the following three types of image feature amounts extractable by the feature amount classification processing unit 302 from at least one of the two images.

FIG. 4A Point spread function (PSF) (=function indicating a blur mode) FIG. 4B Luminance distribution information FIG. 4C Noise information "FIG. 4A Point spread function (PSF) (=function indicating a blur mode)" is a point spread function (PSF) being a function indicating a blur amount of an image.

As illustrated in the specific example of FIG. 4A2, this is a function that indicates the degree of spreading around pixel values at a certain pixel position, that is, a blur amount.

Note that this point spread function is an image feature amount obtainable from either one of the visible light image 211 and the fluorescence image 212.

"FIG. 4B Luminance distribution information" is distribution information of the luminance value of each pixel in the image. A specific example of FIG. 4B2 illustrates a graph (luminance distribution graph) setting pixel positions on the horizontal axis and luminance values on the vertical axis.

The example illustrated in the figure indicates low luminance value on the left side of the graph and high luminance values on the right side. Such a luminance distribution is, for example, a luminance distribution corresponding to an edge region such as a boundary of a subject or the like.

Note that this type of luminance distribution information is an image feature amount obtainable from either one of the visible light image 211 and the fluorescence image 212.

"FIG. 4C Noise information" is information indicating noise included in an image. An image photographed by the camera contains a certain level of noise.

A specific example of FIG. 4C2 illustrates a graph (noise distribution graph) setting pixel positions on the horizontal axis and pixel values on the vertical axis.

As illustrated in this graph, the pixel value is a value obtained by adding a predetermined amount of noise to original color or luminance of the subject. Note that there are various types of noise such as high frequency noise, low frequency noise and so on.

Note that this noise information is also an image feature amount obtainable from either one of the visible light image 211 and the fluorescence image 212.

These three types of image feature amounts illustrated in FIGS. 4A1, 4A2, 4B1, 4B2, 4C1, and 4C2 are examples of feature amount data obtained from at least one of the visible light image 211 or the fluorescence image 212 by the feature amount classification processing unit 302.

The feature amount classification processing unit 302 obtains at least any one of the three types of image feature amounts illustrated in FIGS. 4A1, 4A2, 4B1, 4B2, 4C1, and 4C2 from at least one of the visible light image 211 or the fluorescence image 212.

An image correction unit 325 executes image correction processing as image quality enhancement processing on the visible light image 211 and the fluorescence image 212 on the basis of the obtained feature amount, and then, generates and outputs the corrected visible light image 221 and the corrected fluorescence image 222 with enhanced image quality.

Note that, in the configuration illustrated in FIG. 3, the imaging unit 106 is configured to photograph the visible-fluorescence mixture image 210 including both the photographing light in the visible light region constituting the ordinary color image and the photographing light in the fluorescent region and input the visible-fluorescence mixture image 210 to the image processing unit 120.

The image processing unit 120 causes the image separating unit 301 to generate two images, namely, the visible light image 211 and the fluorescence image 212, from the visible-fluorescence mixture image 210.

Next, with reference to FIG. 5, description will be given on configuration and processing of the image processing unit 120 in a case where the imaging unit 106 alternately and separately photographs the visible light image being an ordinary color image, and the fluorescence image, and inputs the images to the image processing unit 120.

Figure 5:
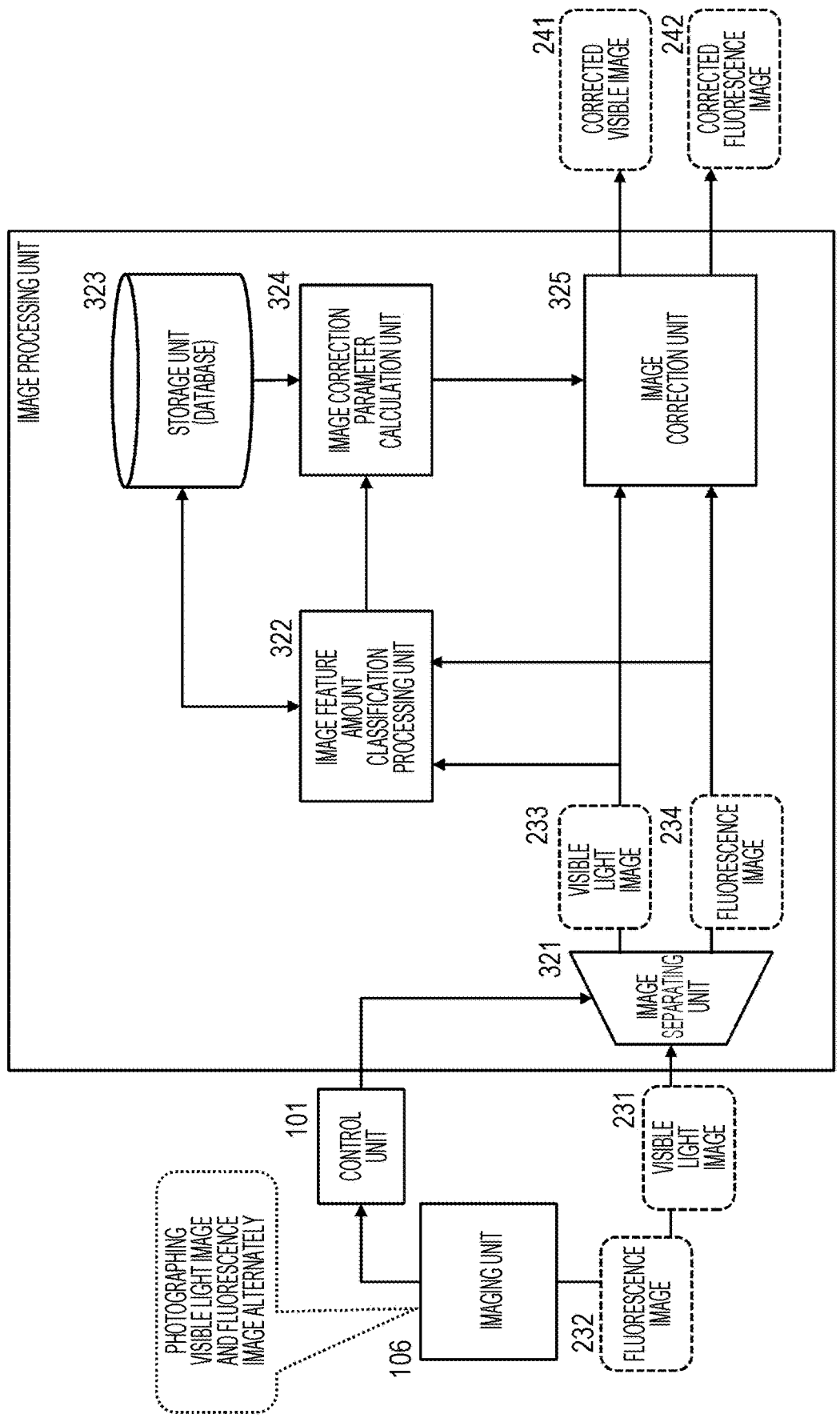
FIG. 5 is a diagram illustrating configuration and processing of an image processing unit.

The imaging unit 106 illustrated in FIG. 5 photographs a visible light image 231 corresponding to an ordinary color image and a fluorescence image 232 separately and alternately and inputs the images to the image processing unit 120.

The image processing unit 120 sequentially inputs the visible light image 231 and the fluorescence image 232, then generates and outputs a corrected visible light image 241 and a corrected fluorescence image 242 respectively obtained by applying image quality enhancement processing on each of these images.

Processing executed by the image processing unit 120 will be described.

The visible light image 231 and the fluorescence image 232 sequentially photographed by the imaging unit 106 are input to an image separating unit 321 of the image processing unit 120.

Under the control of the control unit 101, the image separating unit 321 separates an input image from the imaging unit 106 into a visible light image 233 and a fluorescence image 234 by time sharing processing.

For example, an image input at a timing t0 is a visible light image, an input image at a next timing t1 is a fluorescence image, t2=visible light image, t3=fluorescence image, and so on.

The control unit 101 controls the image separating unit 321 in accordance with an image photographing timing of the imaging unit 106 and performs processing of separate the visible light image 233 and the fluorescence image 234 from each other.

The visible light image 233 and the fluorescence image 234 generated by image separation processing on the image separating unit 321 are input to a feature amount classification processing unit 322 and the image correction unit 325.

The feature amount classification processing unit 322 inputs the visible light image 233 and the fluorescence image 234, extracts an image feature amount from these images, executes classification processing based on the extracted feature amount and stores data into a storage unit (database), while inputting a feature amount data classification result to an image correction parameter calculation unit 324.

Note that classification processing is classification processing in general machine learning.

Herein, the classification represents classification for determining the correction mode as to what types of image correction is effective for image quality enhancement processing on the basis of the feature amount obtained from the image.

Note that training data to be applied to this classification is stored in a storage unit (database) 323, and the feature amount classification processing unit 322 uses the training data stored in the storage unit (database) 303, and determines an optimum correction mode for the image quality enhancement processing for the input image (the visible light image 233 and the fluorescence image 234).

The determination information of the correction mode is input to the image correction parameter calculation unit 324.

The image correction parameter calculation unit 324 uses the correction mode determination information input from the feature amount classification processing unit 322 and training data stored in the storage unit (database) 323 to determine the image correction parameter to be used for performing image quality enhancement processing on the visible light image 233 and the fluorescence image 234.

The determined image correction parameter is input to the image correction unit 325.

The image correction unit 325 applies the image correction parameter input from the image correction parameter calculation unit 324 to execute image correction processing on the visible light image 233 and the fluorescence image 234, and then, generates and outputs the corrected visible light image 241 and the corrected fluorescence image 242 that have undergone image quality enhancement processing.

The feature amount data obtained from the visible light image 233 and the fluorescence image 234 by the feature amount classification processing unit 322 is the data illustrated in FIGS. 4A1, 4A2, 4B1, 4B2, 4C1, and 4C2 described above and the following data, for example.

FIG. 4A Point spread function (PSF) (=function indicating a blur mode)

FIG. 4B Luminance distribution information

FIG. 4C Noise information

These three image feature amounts illustrated in FIGS. 4A1, 4A2, 4B1, 4B2, 4C1, and 4C2 are examples of feature amount data obtained from at least one of the visible light image 233 or the fluorescence image 234 by the feature amount classification processing unit 322.

The image correction unit 325 executes image correction processing as image quality enhancement processing on the visible light image 233 and the fluorescence image 234 on the basis of the obtained feature amount, and then, generates and outputs the corrected visible light image 241 and the corrected fluorescence image 242 with enhanced image quality.

[3. Configuration for executing image quality enhancement processing applying blur mode information (PSF information) as image feature amount]

As described above with reference to FIGS. 4A1, 4A2, 4B1, 4B2, 4C1, and 4C2, the feature amount classification processing unit of the image processing unit illustrated in FIGS. 3 and 5 extracts the following image feature amount from the visible light image and the fluorescence image, for example.

FIG. 4A Point spread function (PSF) (=function indicating a blur mode)

FIG. 4B Luminance distribution information

FIG. 4C Noise information

The image correction unit of the image processing unit illustrated in FIG. 3 or FIG. 5 executes image correction processing for image quality enhancement onto a visible light image or a fluorescence image in accordance with a correction mode or a correction parameter determined on the basis of these feature amounts.

Hereinafter, a configuration for executing image quality enhancement processing applying blur mode information (PSF information) as image feature amount will be described.

Figure 6:
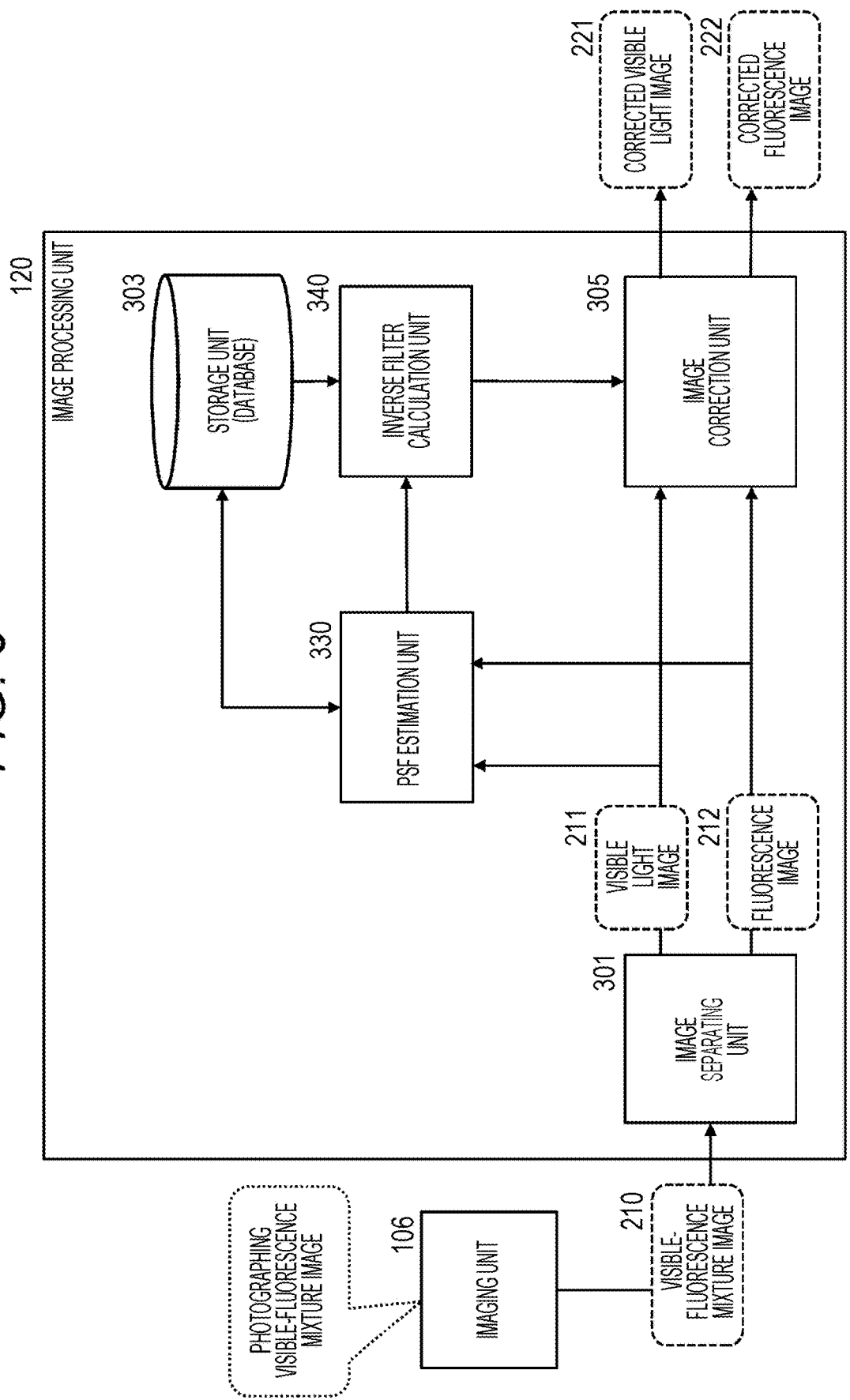
FIG. 6 is a diagram illustrating configuration and processing of an image processing unit.

FIG. 6 is a configuration similar to the configuration of the image processing unit 120 described above with reference to FIG. 3.

That is, the imaging unit 106 photographs the visible-fluorescence mixture image 210 including both the photographing light of the visible light region constituting the ordinary color image and the photographing light of the fluorescent region. The visible-fluorescence mixture image 210 photographed by the imaging unit 106 is input to the image processing unit 120.

The image processing unit 120 inputs the visible-fluorescence mixture image 210, generates and outputs a corrected visible light image 221 and a corrected fluorescence image 222 that have undergone image quality enhancement processing.

The image processing unit 120 illustrated in FIG. 6 has a configuration in which the feature amount classification processing unit 302 of the image processing unit 120 illustrated in FIG. 3 is replaced with a PSF estimation unit 330, and further the image correction parameter calculation unit 304 is replaced with an inverse filter calculation unit 340.

Processing executed by the image processing unit 120 illustrated in FIG. 6 will be described.

The image processing unit 120 first inputs the visible-fluorescence mixture image 210 photographed by the imaging unit 106 to an image separating unit 301, and then, separates the visible-fluorescence mixture image 210 into a visible light image 211 constituted with a visible light component similar to an ordinary RGB color image, and a fluorescence image 212 constituted with a fluorescent component alone.

This is executed by matrix operation applying separation matrix, for example.

The visible light image 211 and the fluorescence image 212 generated by image separation processing in the image separating unit 301 are input to the PSF estimation unit 330 and the image correction unit 305.

The PSF estimation unit 330 inputs the visible light image 211 and the fluorescence image 212, extracts a point spread function (PSF) as blur mode information as an image feature amount from these images, and executes classification processing based on the extracted blur mode information (PSF information), and stores data in the storage unit (database), while inputting a classification result of the blur mode information (PSF information) to the inverse filter calculation unit 340.

Note that classification processing is classification processing in general machine learning.

Herein, the classification represents classification for determining the correction mode as to what types of image correction is effective for image quality enhancement processing on the basis of the feature amount obtained from the image.

Note that training data to be applied to this classification is stored in the storage unit (database) 303, and the PSF estimation unit 330 uses the training data stored in the storage unit (database) 303, and determines an optimum correction mode for the image quality enhancement processing for the input image (the visible light image 211 and the fluorescence image 212).

The determination information of the correction mode is input to the inverse filter calculation unit 340.

The inverse filter calculation unit 340 uses the correction mode determination information input from the PSF estimation unit 330 and the training data stored in the storage unit (database) 303 to generate an inverse filter for performing image quality enhancement processing of the visible light image 211 and the fluorescence image 212, that is, an inverse filter such as a Wiener filter, for example, to be applied to suppress blur.

The generated inverse filter is input to the image correction unit 305.

The image correction unit 305 applies the inverse filter input from the inverse filter calculation unit 340 to execute image correction processing on the visible light image 211 and the fluorescence image 212, and then, generates and outputs the corrected visible light image 221 and the corrected fluorescence image 222 that have undergone image quality enhancement processing.

A specific example of processing executed by the PSF estimation unit 330, the inverse filter calculation unit 340, and the image correction unit 305 will be described with reference to FIG. 7.

Figure 7:
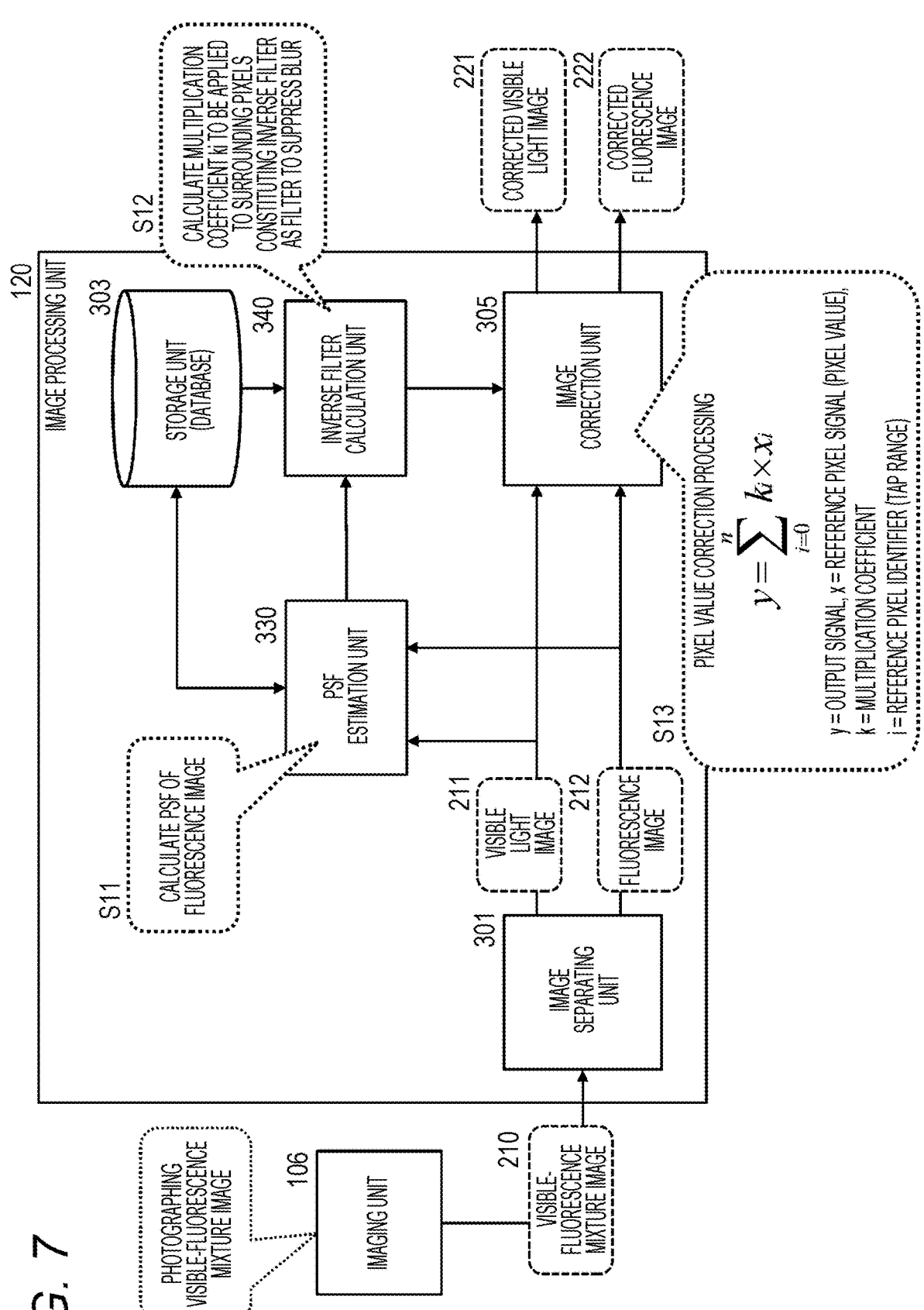
FIG. 7 is a diagram illustrating configuration and processing of an image processing unit.

Note that the example described with reference to FIG. 7 is a processing example in which the correction target is a fluorescence image.

The PSF estimation unit 330 extracts a point spread function (PSF) (=a function indicating a mode indicating a blur mode) as the image feature amount from the fluorescence image 212 and outputs the extracted function to the inverse filter calculation unit 340.

The inverse filter calculation unit 340 and the image correction unit 305 executes processing of generating an inverse filter to be applied to image correction processing for image quality enhancement for the fluorescence image 212 and pixel value correction processing applying the inverse filter on the basis of the point spread function (PSF) (=a function indicating a mode indicating a blur mode) extracted by the PSF estimation unit 330 from the fluorescence image 212.

FIG. 7 illustrates individual processing to be executed by the PSF estimation unit 330, the inverse filter calculation unit 340, and the image correction unit 305.

As illustrated in FIG. 7, the PSF estimation unit 330 obtains a point spread function (PSF) (=a function indicating a mode indicating a blur mode) as an image feature amount from the fluorescence image 212 in step S11.

The point spread function (PSF) (=function indicating the blur mode) is a function indicating the blur amount of an image as described above with reference to FIG. 4A.

As illustrated in the specific example of FIG. 4A2, this is a function that indicates the degree of spreading around pixel values at a certain pixel position, that is, a blur amount.

Note that herein a point spread function (PSF) is obtained using the fluorescence image 212.

The point spread function (PSF) information extracted from the fluorescence image 212 by the PSF estimation unit 330 is input to the inverse filter calculation unit 340.

The inverse filter calculation unit 340 calculates a coefficient constituting the inverse filter being a filter for suppressing blur as a correction parameter to be applied to correction processing on the basis of the point spread function (PSF) information extracted from the fluorescence image 212 by the PSF estimation unit 330 in step S12. That is, a multiplication coefficient to be applied to reference pixels surrounding the correction target pixel is calculated.

An example of correction parameter calculation processing in the inverse filter calculation unit 340 will be described with reference to FIGS. 8A, 8B, 8C, 9A, 9B, and 9C.

FIGS. 8A, 8B, and 8C includes the following diagrams.

FIG. 8A Example of pixel value distribution on an image before correction

FIG. 8B Example of tap setting and correction parameter (multiplication coefficient Ki)

FIG. 8C Example of pixel value distribution on image after correction

A This example of pixel value distribution on an image before correction is an example of pixel value distribution on a fluorescence image as a correction target image.

As described above, in a case where an internal image of a living body is photographed, for example, the amount of scattered light rays increases in a fluorescence image, leading to an increase in the blur amount. As illustrated in FIG. 8A, the pixel value distribution is a distribution that gently reflects the luminance of the subject resulting in an image with large amount of blur.

The inverse filter calculation unit 340 performs setting (tap selection) of a reference region for performing image correction of correcting a fluorescence image with a large amount of blur like this to be a clear image with little blur, and further calculates a coefficient constituting an inverse filter as a filter for blur suppression, that is, calculates a multiplication coefficient $k_i$ to be applied to reference pixels surrounding the correction target pixel.

Specifically, for example, the larger (wider) the blur amount of the fluorescence image 212, the wider range reference pixel region (tap region) is set so as to determine the multiplication coefficient $k_i$ as an effective correction parameter for suppressing the blur of the fluorescence image 212.

"FIG. 8B Example of tap setting and the correction parameter (multiplication coefficient Ki)" in FIGS. 8A, 8B, and 8C illustrate positions of the surrounding reference pixels for correcting the pixel value of the correction target pixel as the correction target pixel as a center, and a value of multiplication coefficient ki for each of the reference pixels.

The example illustrated in the figure is a case of including 3×3=9 pixels arranged as the correction target pixel as a center. 0, −1, and 9 illustrated at nine pixel positions are multiplication coefficients ki being correction parameters calculated by the inverse filter calculation unit 340. Note that i is a pixel position identifier indicating a pixel position.

In the tap selection processing, the pixel position referred to for calculating a correction pixel value for the correction target pixel is selected as a tap position. In the example illustrated in the figure, a pixel position set to −1 or 9 is a tap.

Moreover, the inverse filter calculation unit 340 calculates the multiplication coefficient ki to be multiplied by the pixel value of the tap position. This corresponds to −1 or 9 illustrated in FIG. 8B.

Note that the filter calculated by the inverse filter calculation unit 340 is a filter for suppressing blur, specifically, for example, a Wiener filter or the like is generated.

The inverse filter generated by the inverse filter calculation unit 340 is input to the image correction unit 305.

The image correction unit 305 calculates the correction pixel value of the fluorescence image 212 using the inverse filter generated by the inverse filter calculation unit 340. Specifically, a correction pixel value y of the correction target pixel is calculated by applying the following correction pixel value calculation formula (Formula 1) illustrated in step S13 in FIG. 7.

The correction pixel value y is calculated by the following (Formula 1).

[Mathematical Expression 1]

$$y = \sum_{i=0}^{n} k_i \times x_i \quad \text{(Formula 1)}$$

Note that In the above (Formula 1), each of symbols has the following meaning.
y: correction pixel value of correction target pixel
$x_i$: pixel value of reference pixel
i: pixel identifier of reference pixel
$k_i$: multiplication coefficient corresponding to reference pixel i The correction target pixel is a pixel at a center position of 3×3=9 pixels illustrated in FIG. 8B, for example.

The reference pixel is each of pixels of 3×3=9 pixels, and xi is a pixel value of each of the pixels. i is the identifier of the pixel. In the case nine pixels are referred to, n=8 is set, and the correction pixel value T is calculated using the pixel value of each of the pixels of i=0 to 8.

ki is a multiplication coefficient for the pixel value xi set at each of pixel positions i.

Pixel values of the correction target pixels are calculated in accordance with the above (Formula 1).

Note that the tap setting and the correction parameter (multiplication coefficient) setting illustrated in FIG. 8B are mere examples, and the tap and the correction parameter are changed to various settings in accordance with the feature amount.

The image correction unit 305 sequentially calculates the correction pixel values of all of the constituent pixels of the fluorescence image 212 in accordance with the above-described (Formula 1), and generates and outputs the calculated configured corrected fluorescence image 222.

An example of pixel value distribution of the corrected fluorescence image 222 is illustrated in FIG. 8C.

The pixel value distribution of the corrected fluorescence image 222 is an image with steeper gradient of the pixel value change with suppressed blur, as compared with the pixel value distribution of the fluorescence image before correction illustrated in FIG. 8A.

This is a result of performing pixel value correction using an inverse filter with a coefficient set as a blur suppression filter.

In this manner, the pixel value of the fluorescence image is corrected using the PSF information being the feature amount indicating the blur mode of the fluorescence image, making it possible to perform image quality enhancement on a fluorescence image having a large amount of blur, that is, possible to generate and output the corrected fluorescence image 222 with reduced blur amount.

Note that the examples illustrated in FIGS. 8A and 8B are examples of tap setting and a setting of correction parameter (multiplication coefficient ki) in a case where the expansion of blur is relatively small.

The tap setting and the setting of the correction parameter (multiplication coefficient ki) are changed in accordance with the PSF obtained as the feature amount, that is, the blur mode.

FIGS. 9A, 9B, and 9C illustrate examples of tap setting and the setting of the correction parameter (multiplication coefficient Ki) in a case where the expansion of blur is relatively large.

As illustrated in FIGS. 9A and 9B, in a case where the blur amount is large, the tap setting is performed to increase the pixel region to be used as reference determination, so as to perform processing of determining the correction pixel value on the basis of the pixel value of the reference pixel in the wider range.

In this manner, the reference pixel region selection processing applied to the correction processing, that is, the tap selection processing is executed, and correction parameters (multiplication coefficients) are calculated to perform correction processing on the basis of the point spread function (PSF) information calculated by the PSF estimation unit 330 set as the feature amount classification processing unit 302, making it possible to perform optimum pixel value correction according to the blur mode and to generate a high quality corrected fluorescence image with reduced blur.

Next, referring to FIG. 10, description will be given on configuration and processing of the image processing unit 120 in a case where the imaging unit 106 photographs the visible light image being an ordinary color image and a fluorescence image separately and alternately and inputs the images to the image processing unit 120.

Figure 10:
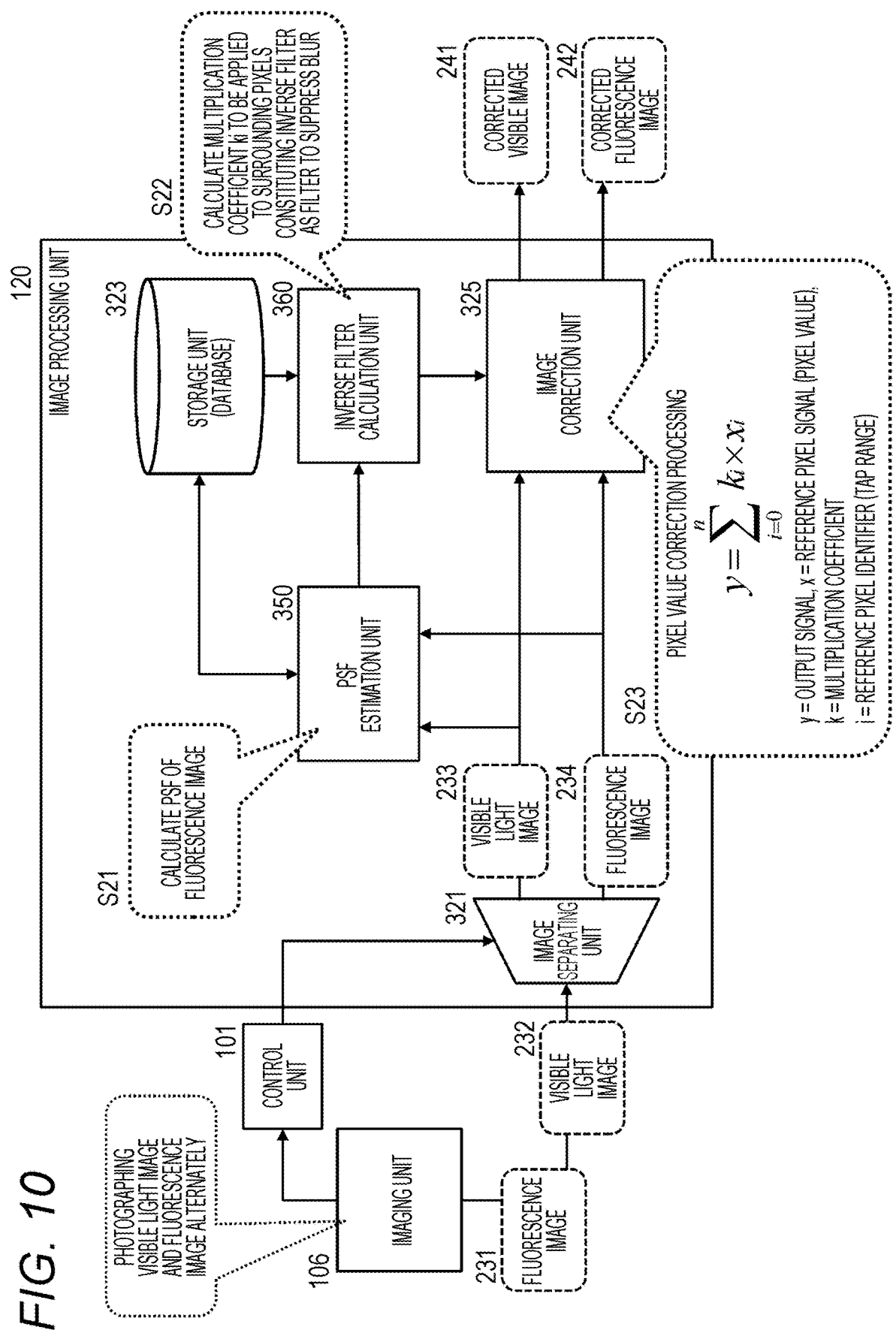
FIG. 10 is a diagram illustrating configuration and processing of an image processing unit.

The configuration of the image processing apparatus illustrated in FIG. 10 is similar to the configuration of the image processing apparatus with reference to FIG. 5.

The imaging unit 106 illustrated in FIG. 10 photographs the visible light image 231 corresponding to ordinary color image and the fluorescence image 232 separately and alternately and inputs the images to the image processing unit 120.

The image processing unit 120 sequentially inputs the visible light image 231 and the fluorescence image 232, then generates and outputs a corrected visible light image 241 and a corrected fluorescence image 242 respectively obtained by applying image quality enhancement processing on each of these images.

The image processing unit 120 illustrated in FIG. 10 has a configuration in which the feature amount classification processing unit 322 of the image processing unit 120 illustrated in FIG. 5 is replaced with a PSF estimation unit 350, and furthermore the image correction parameter calculation unit 324 is replaced with an inverse filter calculation unit 360.

Processing executed by the image processing unit 120 illustrated in FIG. 10 will be described.

The visible light image 231 and the fluorescence image 232 sequentially photographed by the imaging unit 106 are input to an image separating unit 321 of the image processing unit 120.

Under the control of the control unit 101, the image separating unit 321 separates an input image from the imaging unit 106 into a visible light image 233 and a fluorescence image 234 by time sharing processing.

An example of setting is: an image input at a timing t0 is a visible light image, an input image at a next timing t1 is a fluorescence image, t2=visible light image, t3=fluorescence image, and so on.

The control unit 101 controls the image separating unit 321 in accordance with an image photographing timing of the imaging unit 106 and performs processing of separate the visible light image 233 and the fluorescence image 234 from each other.

The visible light image 233 and the fluorescence image 234 generated by image separation processing in the image separating unit 301 are input to the PSF estimation unit 350 and the image correction unit 325.

The PSF estimation unit 350 inputs the visible light image 233 and the fluorescence image 234, extracts a point spread function (PSF) as blur mode information as an image feature amount from these images, and executes classification processing based on the extracted blur mode information (PSF information), and stores data in the storage unit (database), while inputting a classification result of the blur mode information (PSF information) to the inverse filter calculation unit 360.

Note that classification processing is classification processing in general machine learning.

Herein, the classification represents classification for determining the correction mode as to what types of image correction is effective for image quality enhancement processing on the basis of the feature amount obtained from the image.

Note that training data to be applied to this classification is stored in the storage unit (database) 323, and the PSF estimation unit 350 uses the training data stored in the storage unit (database) 323, and determines an optimum correction mode for the image quality enhancement processing for the input image (the visible light image 233 and the fluorescence image 234).

The determination information of the correction mode is input to the inverse filter calculation unit 360.

The inverse filter calculation unit 360 uses the correction mode determination information input from the PSF estimation unit 350 and the training data stored in the storage unit (database) 323 to generate an inverse filter for performing image quality enhancement processing of the visible light image 233 and the fluorescence image 234, that is, an inverse filter such as a Wiener filter, for example, to be applied to suppress blur.

The generated inverse filter is input to the image correction unit 325.

The image correction unit 325 applies the inverse filter input from the inverse filter calculation unit 360 to execute image correction processing on the visible light image 233 and the fluorescence image 234, and then, generates and outputs the corrected visible light image 241 and the corrected fluorescence image 242 that have undergone image quality enhancement processing.

A specific example of processing executed by the PSF estimation unit 350, the inverse filter calculation unit 360, and the image correction unit 325 will be described with reference to the processing steps S21 to S23 illustrated in FIG. 10.

Note that the example described with reference to FIG. 10 is a processing example in which the correction target is a fluorescence image.

FIG. 10 illustrates processing to be executed by the PSF estimation unit 350, the inverse filter calculation unit 360, and the image correction unit 325, as steps S21 to S23, respectively.

As illustrated in FIG. 10, the PSF estimation unit 350 obtains a point spread function (PSF) (=a function indicating a mode indicating a blur mode) as an image feature amount from the fluorescence image 234 in step S21.

The point spread function (PSF) (=function indicating the blur mode) is a function indicating the blur amount of an image as described above with reference to FIG. 4A.

As illustrated in the specific example of FIG. 4A2, this is a function that indicates the degree of spreading around pixel values at a certain pixel position, that is, a blur amount.

Note that herein a point spread function (PSF) is obtained using the fluorescence image 234.

The point spread function (PSF) information extracted from the fluorescence image 234 by the PSF estimation unit 350 is input to the inverse filter calculation unit 360.

The inverse filter calculation unit 360 calculates a coefficient constituting the inverse filter being a filter for suppressing blur as a correction parameter to be applied to correction processing on the basis of the point spread function (PSF) information extracted from the fluorescence image 234 by the PSF estimation unit 350 in step S22. That is, a multiplication coefficient to be applied to reference pixels surrounding the correction target pixel is calculated.

The correction parameter calculation processing in the inverse filter calculation unit 360 is similar to that described above with reference to FIGS. 8A, 8B, 8C, 9A, 9B, and 9C.

Note that the filter calculated by the inverse filter calculation unit 360 is a filter for suppressing blur, specifically, for example, a Wiener filter or the like is generated.

The inverse filter generated by the inverse filter calculation unit 360 is input to the image correction unit 325.

The image correction unit 325 calculates the correction pixel value of the fluorescence image 234 using the inverse filter generated by the inverse filter calculation unit 360. Specifically, the correction pixel value y of the correction target pixel is calculated by applying the following correction pixel value calculation formula (Formula 2) illustrated in Step S23 of FIG. 10.

The correction pixel value y is calculated by the following (Formula 2).

[Mathematical Expression 2]

$$y = \sum_{i=0}^{n} k_i \times x_i \quad \text{(Formula 2)}$$

Note that in the above (Formula 2), each of symbols has the following meaning.

y: correction pixel value of correction target pixel $x_i$: pixel value of reference pixel i: pixel identifier of reference pixel $k_i$: multiplication coefficient corresponding to reference pixel i The correction target pixel is a pixel at a center position of 3×3=9 pixels illustrated in FIG. 8B, for example.

The reference pixel is each of pixels of 3×3=9 pixels, and xi is a pixel value of each of the pixels. i is the identifier of the pixel. In the case nine pixels are referred to, n=8 is set, and the correction pixel value T is calculated using the pixel value of each of the pixels of i=0 to 8.

ki is a multiplication coefficient for the pixel value xi set at each of pixel positions i.

Pixel values of the correction target pixels are calculated in accordance with the above (Formula 2).

In this manner, the reference pixel region selection processing applied to the correction processing, that is, the tap selection processing is executed, and correction parameters (multiplication coefficients) are calculated to perform correction processing on the basis of the point spread function (PSF) information calculated by the PSF estimation unit 350 set as the feature amount classification processing unit 302, making it possible to perform optimum pixel value correction according to the blur mode and to generate a high quality corrected fluorescence image with reduced blur.

Note that the processing example described with reference to FIGS. 6, 7, 8A, 8B, 8C, 9A, 9B, 9C, and 10 focused on the blur suppression processing on the fluorescence image, while it is also possible to suppress the blur of the visible light image with application of similar processing stages to the visible light image.

[4. Configuration for Executing Image Interpolation Processing and Applying Interpolation Image to Execute Image Correction as Image Quality Enhancement Processing]

Next, a configuration for executing image interpolation processing and applying interpolation image to execute image correction as image quality enhancement processing will be described.

The imaging unit 106 of the image processing apparatus 100 illustrated in FIG. 2 photographs different types of images such as a visible light image, a fluorescence image, or a visible light+fluorescence image.

In a configuration in which the imaging unit 106 executes photographing of different types of images, frame rates enabling outputting a visible light image and a fluorescence image do not always match.

For example, here is assumed a configuration in which the imaging unit 106 alternately photographs the following two types of different images.

(a) visible light image
(b) visible light+fluorescence image

Figure 11:
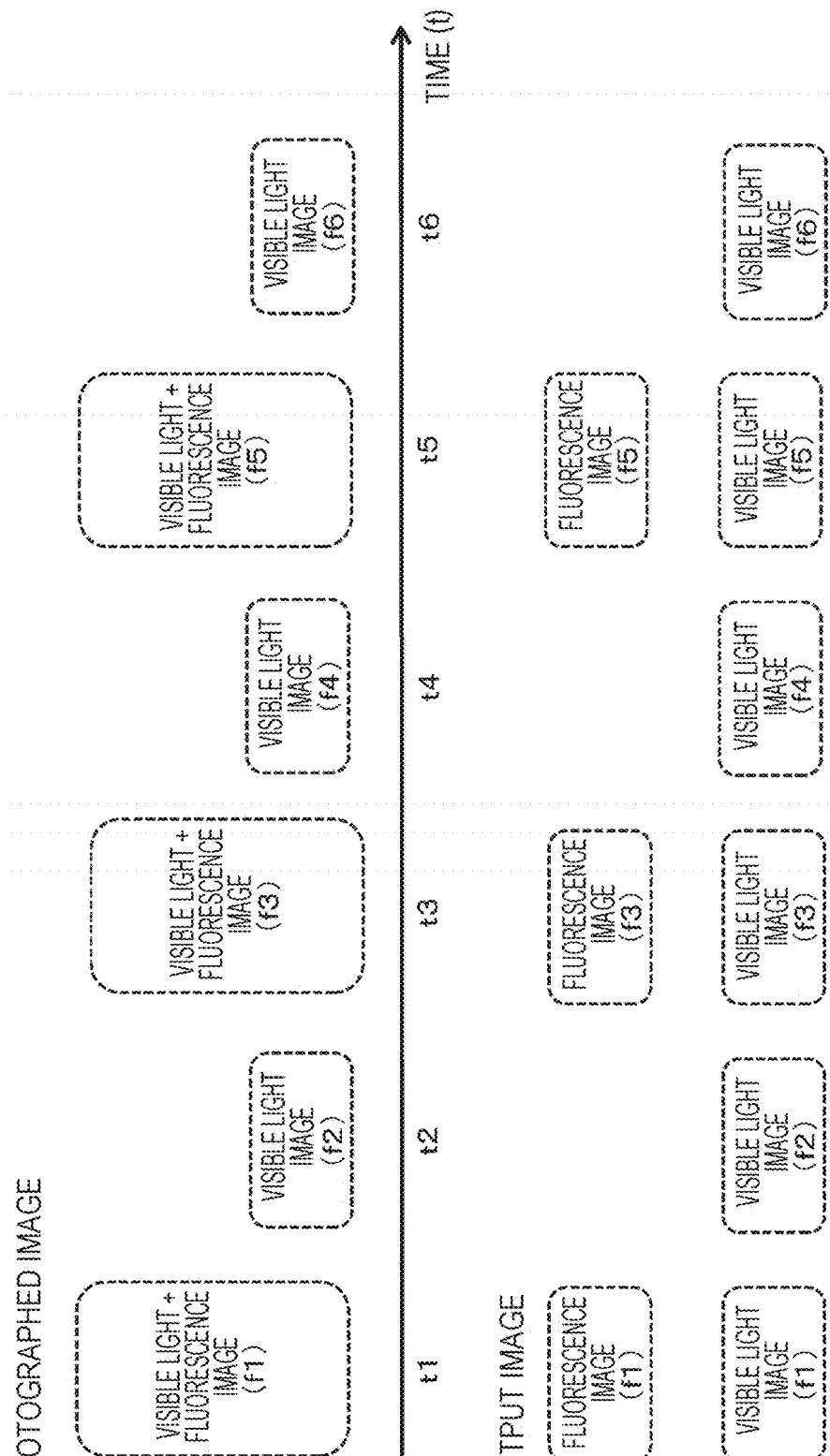
FIGS. 11A and 11B are diagrams illustrating an example of correspondence between photographed images and output images.

Specifically, the configuration has photographed image settings illustrated in FIG. 11A.

The time-series sequence of the photographed image illustrated in FIG. 11A is as follows.

At time t1, an image (f1) of visible light+fluorescence is photographed.

At time t2, a visible light image (f2) is photographed.

At time t3, an image (f3) of visible light+fluorescence is photographed.

At time t4, a visible light image (f4) is photographed.

At time t5, an image (f5) of visible light+fluorescence is photographed.

At time t6, a visible light image (f6) is photographed.

This sequence is repeated thereafter.

When photographing of images is performed with this setting, the image that can be output would be as in the setting of the output images in FIG. 11B. Specifically, the following settings are applied.

At time t1, the visible light image (f1) and a fluorescence image (f1) is obtained by image separation processing of the image (f1) of visible light+fluorescence.

At time t2, a visible light image (f2) alone is output with no output of a fluorescence image.

At time t3, a visible light image (f3) and a fluorescence image (f3) is obtained by image separation processing of the image (f3) of visible light+fluorescence.

At time t4, a visible light image (f4) alone is output with no output of a fluorescence image.

At time t5, a visible light image (f5) and a fluorescence image (f5) is obtained by image separation processing of the image (f5) of visible light+fluorescence.

At time t6, a visible light image (f6) alone is output with no output of a fluorescence image.

This sequence is repeated thereafter.

With image photographing processing illustrated in FIGS. 11A and 11B, the frame rate of the output fluorescence image would be half the frame rate of the visible light image.

Figure 12:
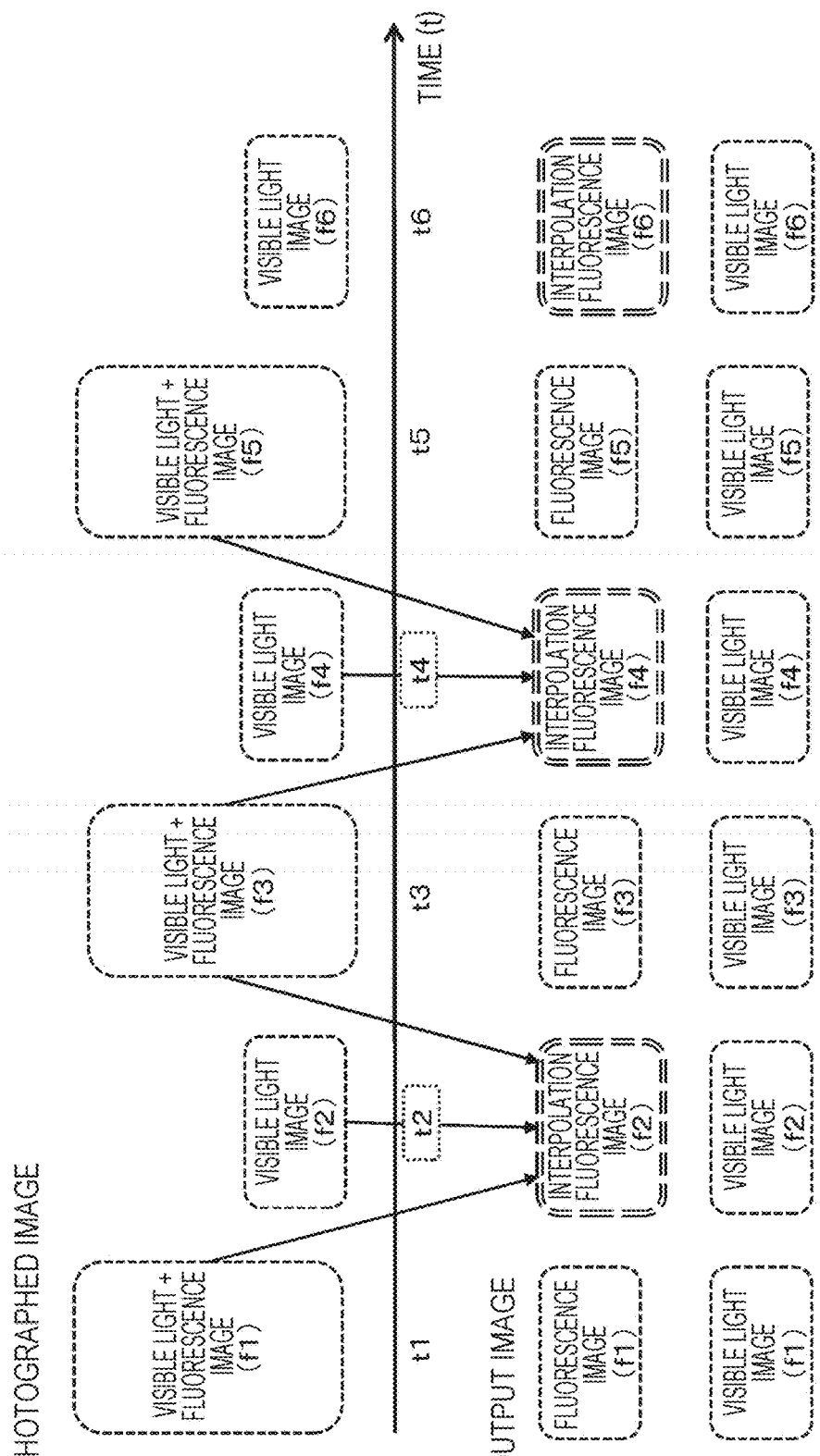
FIGS. 12A and 12B are diagrams illustrating an example of correspondence between photographed images and output images using interpolation images.

With reference to FIGS. 12A and 12B and the subsequent figures, configuration and processing of an image processing apparatus that prevents such a reduction in frame rate and further executes image quality enhancement processing will be described.

FIGS. 12A and 12B is a diagram illustrating image interpolation processing executed by the image processing apparatus of the present exemplary embodiment.

FIG. 12A illustrates the setting of the photographed image similar to that in FIG. 11A, and the time-series sequence of the photographed image is as follows.

At time t1, an image (f1) of visible light+fluorescence is photographed.

At time t2, a visible light image (f2) is photographed.

At time t3, an image (f3) of visible light+fluorescence is photographed.

At time t4, a visible light image (f4) is photographed.

At time t5, an image (f5) of visible light+fluorescence is photographed.

At time t6, a visible light image (f6) is photographed.

This sequence is repeated thereafter.

In the configuration of the present exemplary embodiment, as illustrated in the output image of FIG. 12B, interpolation fluorescence images are generated at each of times, at timings t2, t4, t6 . . . at which no fluorescence image is photographed.

The images correspond to an interpolation fluorescence image (t2), an interpolation fluorescence image (t4), and an interpolation fluorescence image (t6) illustrated in FIG. 12B.

With this image interpolation processing, it is possible to obtain an output image illustrated in FIG. 12B. Specifically, the following settings are applied.

At time t1, the visible light image (f1) and a fluorescence image (f1) is obtained by image separation processing of the image (f1) of visible light+fluorescence.

At time t2, a visible light image (f2) and an interpolation fluorescence image (f2) are output.

At time t3, a visible light image (f3) and a fluorescence image (f3) is obtained by image separation processing of the image (f3) of visible light+fluorescence.

At time t4, a visible light image (f4) and an interpolation fluorescence image (f4) are output.

At time t5, a visible light image (f5) and a fluorescence image (f5) is obtained by image separation processing of the image (f5) of visible light+fluorescence.

At time t6, a visible light image (f6) and an interpolation fluorescence image (f6) are output.

This sequence is repeated thereafter.

With execution of image interpolation processing in this manner, it is possible to set the frame rate of the output fluorescence image to be the same as the frame rate of the visible light image.

A configuration example and processing of an image processing apparatus having an image processing unit that performs image interpolation processing and image quality enhancement processing will be described with reference to FIG. 13.

The imaging unit 106 of an image processing apparatus 400 illustrated in FIG. 13 photographs an image with the photographing sequence of the photographed image described with reference to FIG. 12A.

Figure 13:
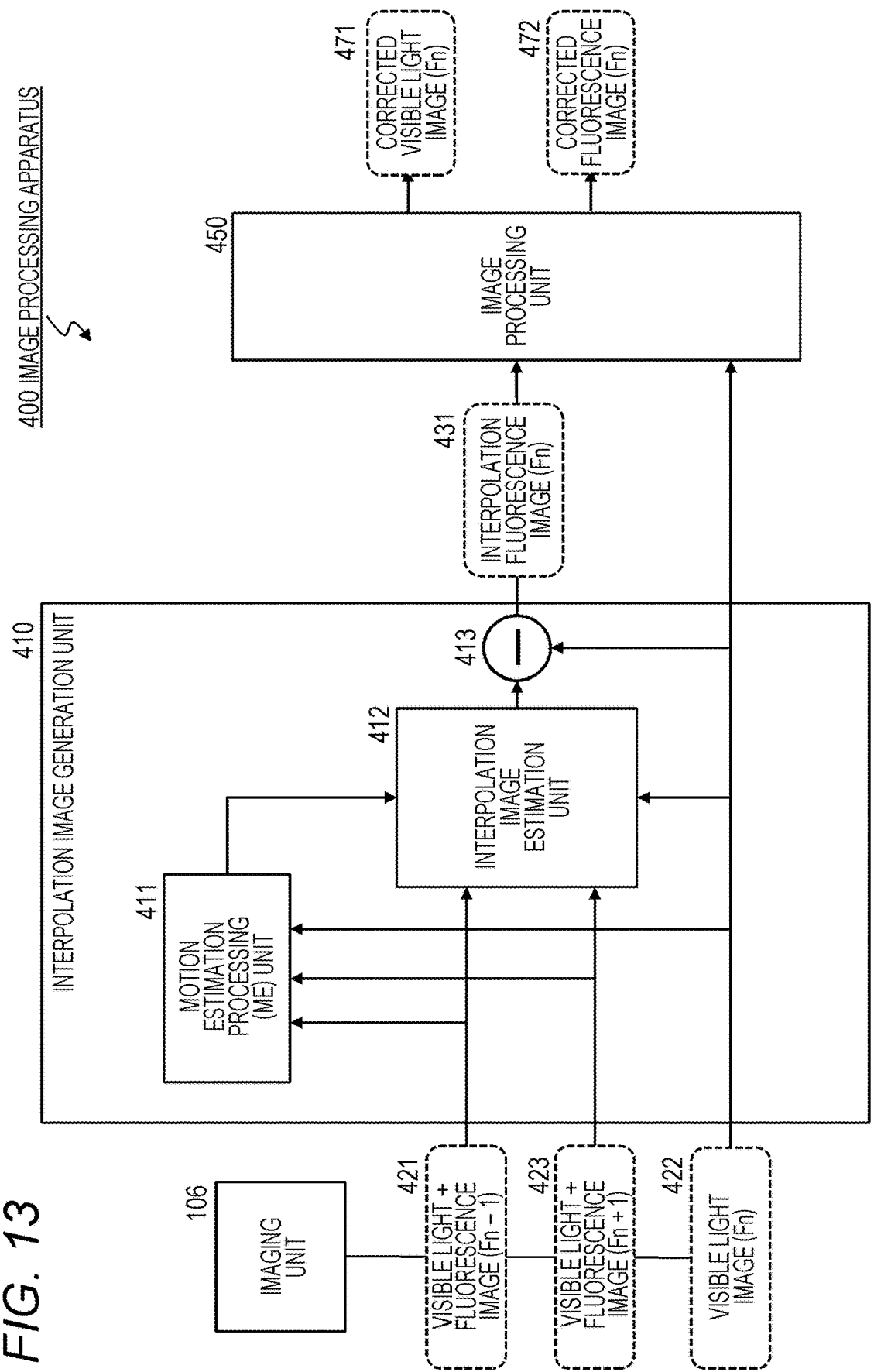
FIG. 13 is a diagram illustrating a configuration example of an image processing apparatus.

FIG. 13 illustrates the following three time-series photographed image frames.

(a) Photographed image frame at time t (n−1)=an image (Fn−1) 421 of visible light+fluorescence, (b) Photographed image frame at time t (n)=visible light image (Fn) 422, and (c) Photographed image frame at time t (n+1)=an image (Fn+1) 423 of visible light+fluorescence.

These three consecutive image frames 421 to 423 are input to an interpolation image generation unit 410.

The interpolation image generation unit 410 includes a motion estimation processing (ME) unit 411, an interpolation image estimation unit 412, and a subtraction unit 413.

The motion estimation processing (ME) unit 411 inputs three image frames 421 to 423, performs motion estimation (ME) between these image frames, and inputs motion information to the interpolation image estimation unit 412.

The three image frames 421 to 423 are images photographed in accordance with a photographing sequence of a photographed pixel eyebrow of FIG. 12A, and are photographed at different photographing timings. Accordingly, a shift occurs in the position of the subject included between individual images due to motion, blur or the like of the subject.

The motion estimation processing (ME) unit 411 calculates the amount of subject position shift between the three image frames 421 to 423 and inputs this as motion information to the interpolation image estimation unit 412.

The interpolation image estimation unit 412 inputs three image frames 421 to 423 and inputs motion information of these three images from the motion estimation processing (ME) unit 411.

The interpolation image estimation unit 412 applies the motion information of the three images input from the motion estimation processing (ME) unit 411, and performs alignment of the three image frames 421 to 423. That is, this corresponds to execution of alignment processing of suppressing the shift so as to locate a same subject on a same coordinate position of each of the images.

Note that in this alignment processing, the photographed image frame at time t(n)=visible light image (Fn) 422 is set as a reference frame, and processing of achieving a match between subject position of the visible light image photographed at this time t(n) with the subject position of another image frame is executed.

The interpolation image estimation unit 412 blends the three image frames 421 to 423 after the alignment and generates an image (Fn) of visible light+fluorescence, which is a virtual photographed image frame at time t(n).

The image (Fn) of visible light+fluorescence generated by the interpolation image estimation unit 412 is input to the subtraction unit 413.

The subtraction unit 413 perform processing of subtracting the visible light image (Fn) 422 from the image (Fn) of visible light+fluorescence generated by the interpolation image estimation unit 412.

This subtraction processing is used to generate an interpolation fluorescence image (Fn) 431.

The interpolation fluorescence image (Fn) 431 is a virtual image corresponding to the fluorescence image photographed at the photographing timing of time t (n) in which imaging of the fluorescence image is not actually executed.

An interpolation fluorescence image (Fn) 431 which is an estimated image at the photographing timing of the time t(n) and a visible light image (Fn) 422 which is actually photographed at the imaging timing of the time t(n) are input to an image processing unit 450.

Figure 14:
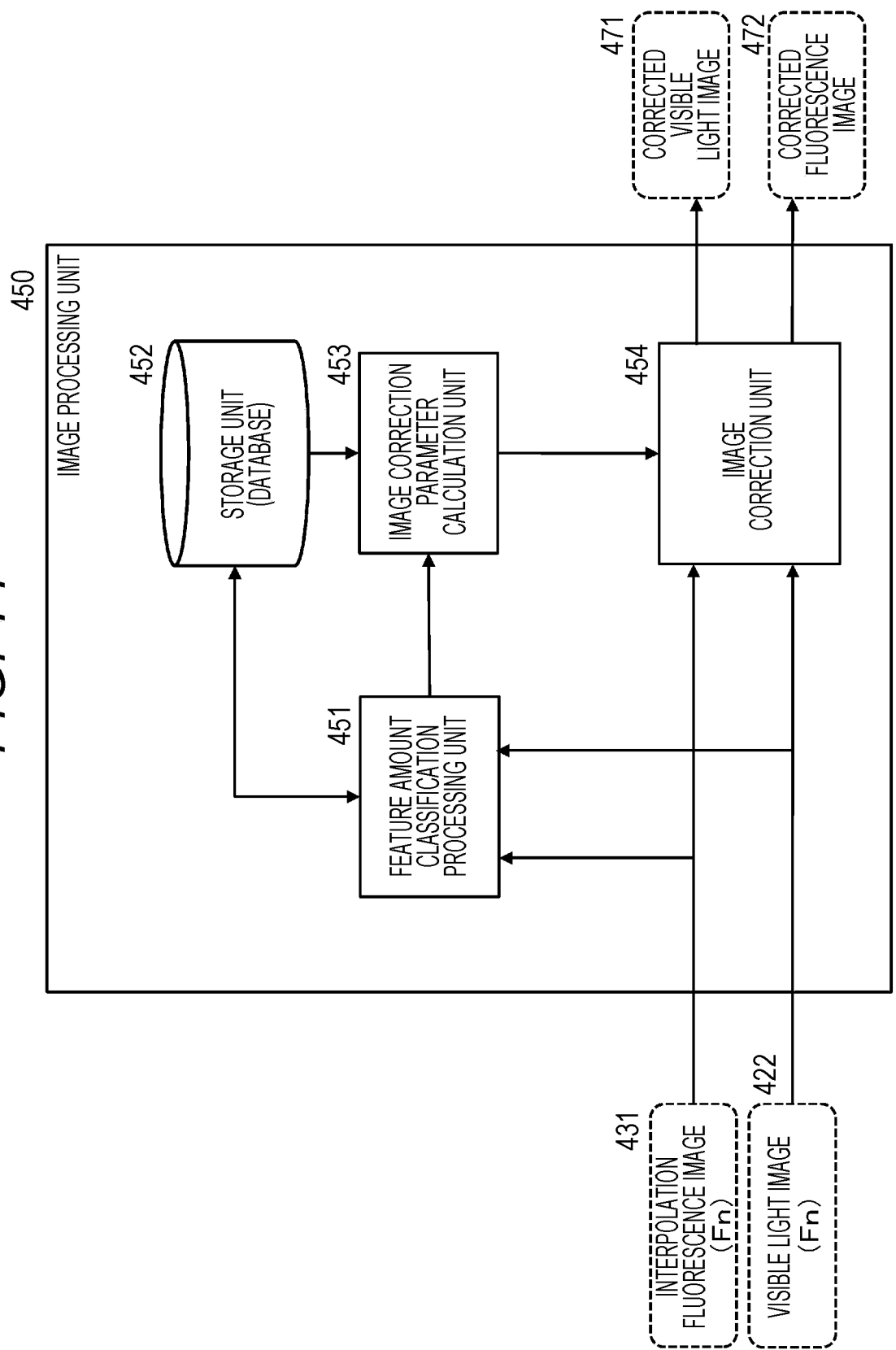
FIG. 14 is a diagram illustrating configuration and processing of an image processing unit.

Configuration and processing of the image processing unit 450 will be described with reference to FIG. 14.

The configuration of the image processing unit 450 illustrated in FIG. 14 corresponds to a configuration in which the image separating unit is omitted from the image processing unit 120 described with reference to FIG. 3, FIG. 5, or the like.

Processing executed by the image processing unit 450 will be described.

The visible light image 422 input from the imaging unit 106 and the interpolation fluorescence image 431 generated by the interpolation image generation unit 410 are input to a feature amount classification processing unit 451 and an image correction unit 454 of the image processing unit 450.

The feature amount classification processing unit 451 inputs the visible light image 422 and the interpolation fluorescence image 431, extracts an image feature amount from these images, executes classification processing based on the extracted feature amount and stores data into a storage unit (database), while inputting a feature amount data classification result to an image correction parameter calculation unit 453.

Note that classification processing is classification processing in general machine learning.

Herein, the classification represents classification for determining the correction mode as to what types of image correction is effective for image quality enhancement processing on the basis of the feature amount obtained from the image.

Note that training data to be applied to this classification is stored in the storage unit (database) 452, and the feature amount classification processing unit 451 uses the training data stored in the storage unit (database) 303, and determines an optimum correction mode for the image quality enhancement processing for the input image (the visible light image 422, the interpolation fluorescence image 431).

The determination information of the correction mode is input to the image correction parameter calculation unit 453.

The image correction parameter calculation unit 453 uses the correction mode determination information input from the feature amount classification processing unit 451 and training data stored in the storage unit (database) 452 to determine the image correction parameter to be used for performing image quality enhancement processing on the visible light image 422 and the interpolation fluorescence image 431.

The determined image correction parameter is input to the image correction unit 454.

The image correction unit 454 applies the image correction parameter input from the image correction parameter calculation unit 453 to execute image correction processing on the visible light image 422 and the interpolation fluorescence image 431, and then, generates and outputs a corrected visible light image 471 and a corrected fluorescence image 472, to which the image quality enhancement processing has been applied.

The feature amount data obtained from the visible light image 422 and the interpolation fluorescence image 431 by the feature amount classification processing unit 451 is the data illustrated in FIGS. 4A1, 4A2, 4B1, 4B2, 4C1, and 4C2 described above and the following data, for example.

FIG. 4A Point spread function (PSF) (=function indicating a blur mode)

FIG. 4B Luminance distribution information

FIG. 4C Noise information

These three image feature amounts illustrated in FIGS. 4A1, 4A2, 4B1, 4B2, 4C1, and 4C2 are examples of feature amount data obtained from at least one of the visible light image 422 or the interpolation fluorescence image 431 by the feature amount classification processing unit 451.

The image correction unit 454 executes image correction processing as image quality enhancement processing on the visible light image 422 and the interpolation fluorescence image 431 on the basis of the obtained feature amount so as to generate and outputs the corrected visible light image 471 and the corrected fluorescence image 472 with enhanced image qualities.

[5. Example of correction processing mode of fluorescence image according to image photographing sequence]

Next, with reference to FIGS. 15A and 15B, an example of a correction processing mode of a fluorescence image according to an image photographing sequence will be described.

As described above with reference to FIGS. 11A, 11B, 12A and 12B, for example, the imaging unit 106 of the image processing apparatus 100 illustrated in FIG. 2 is configured to photograph different types of images, such as a visible light image, a fluorescence image, or a visible light+fluorescence image. These image photographing timing and sequences are assumed to have various settings.

Figure 15:
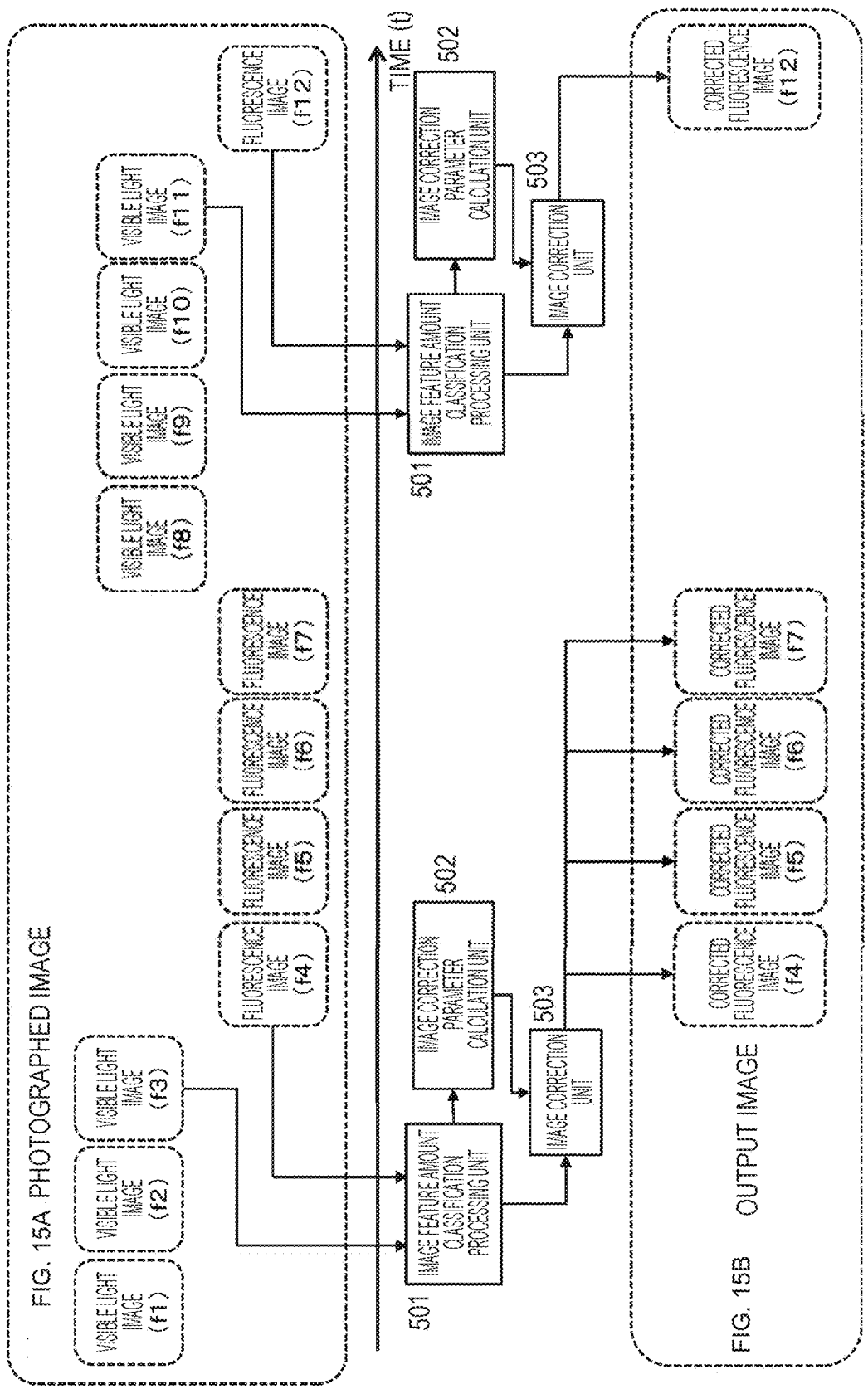
FIGS. 15A and 15B are diagrams illustrating an example of a correspondence with an output image generated by image correction based on a photographed image.

As an example, a photographing sequence as illustrated in a photographed image in FIG. 15A is also assumed.

The sequence of the photographed image illustrated in FIG. 15A is an image photographing sequence of alternately photographing a plurality of visible light image frames and a plurality of fluorescence image frames.

In such an image photographing sequence, for example, the image quality enhancement processing on the fluorescence image (f4) can be performed with application of the configuration of the image processing unit described above with reference to FIG. 5, and with application of the visible light image (f3) being an immediately preceding photographed image frame.

Each of the three image frames of the fluorescence image (f5) to the fluorescence image (f7), however, has no visible light image photographed immediately before the photographing timing of these three image frames.

Accordingly, this makes it difficult to perform image quality enhancement processing applying the two consecutively photographed image frames described with reference to FIG. 5.

In such a case, image correction processing as illustrated in FIGS. 15A and 15B is executed.

Specifically, the image correction mode determined by an image feature amount classification processing unit 501 on the basis of the visible light image (f3) and the fluorescence image (f4) and the correction parameter determined by an image correction parameter calculation unit 502 are applied so as to execute image correction not merely on the image (f4) but also on the fluorescence image (f5) to the fluorescence image (f7) consecutively photographed thereafter.

With this processing, as illustrated in FIG. 15B, it is possible to generate and output the corrected fluorescence image (f4) to the corrected fluorescence image (f7) as output images.

That is, it is possible to generate and output a corrected fluorescence image with higher image quality even when the visible light image and the fluorescence image are not alternately photographed.

[6. Processing Sequence Executed by Image Processing Apparatus]

Next, a processing sequence executed by the image processing apparatus according to the present disclosure will be described with reference to a flowchart illustrated in FIG. 16 and subsequent figures.

[6-1. Basic Sequence of Image Processing]

First, a basic sequence executed by the image processing apparatus according to the present disclosure will be described with reference to a flowchart illustrated in FIG. 16.

Figure 16:
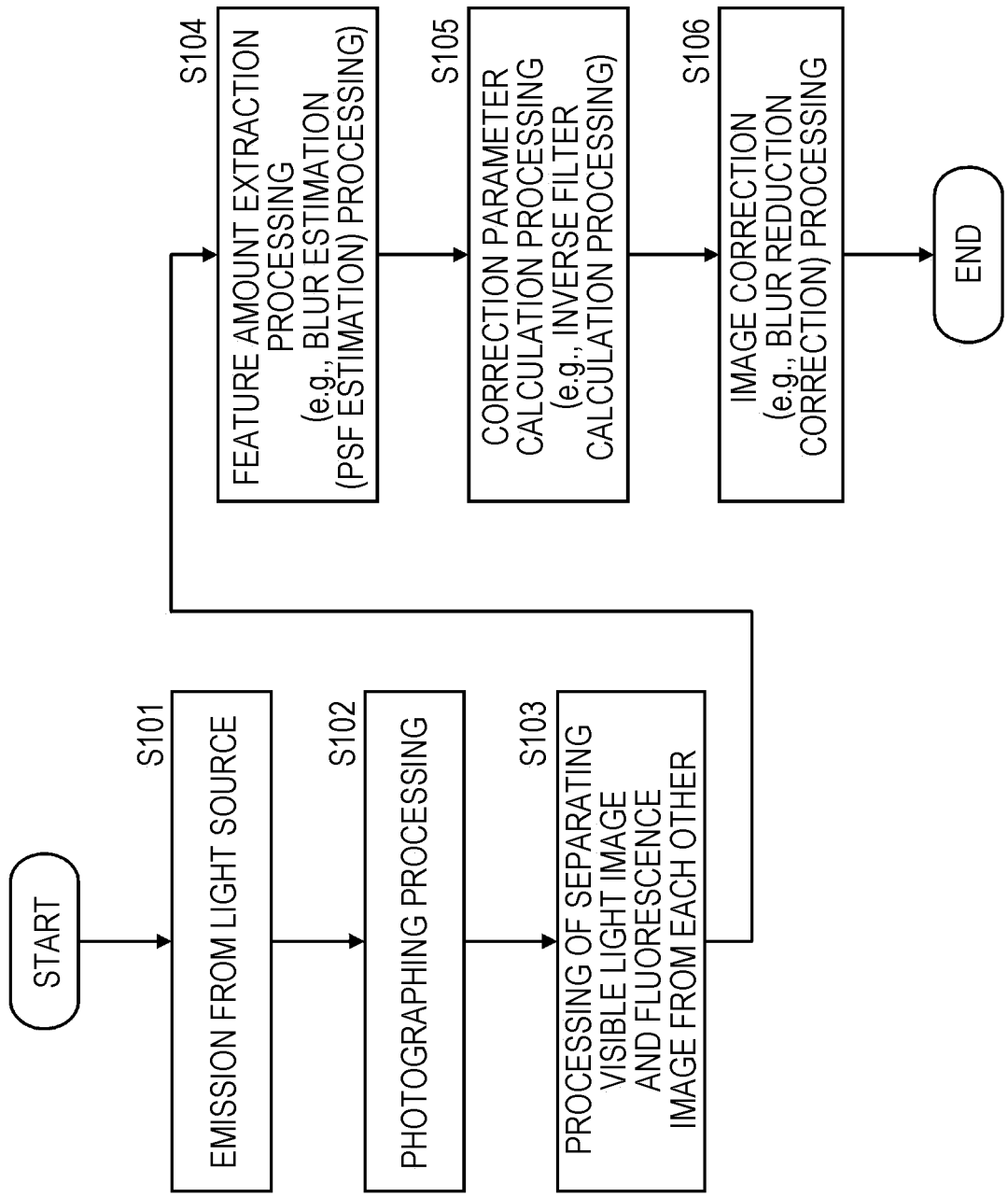
FIG. 16 is a flowchart illustrating a processing sequence executed by an image processing apparatus.

FIG. 16 is a flowchart illustrating a basic processing sequence executed in the image processing apparatus.

The processing according to the flow illustrated in FIG. 16 is executed under the control of a control unit having a program execution function in accordance with a program stored in the storage unit of the image processing apparatus, for example.

Hereinafter, processing of each of steps of the flow illustrated in FIG. 16 will be sequentially described.

(Steps S101 to S102)

Steps S101 to S102 correspond to image photographing processing.

This is, for example, image photographing processing in the imaging unit 106 illustrated in FIGS. 2, 3, 5, or the like.

The photographed image is executed by photographing processing of a visible light image and a fluorescence image, or a visible-fluorescence mixture image.

Emission from light source in step S101 includes visible light emission processing for photographing a visible light image and excitation light emission processing for photographing a fluorescence image.

The photographing processing in step S102 is image photographing processing under this emission from light source, and is photographing processing of a visible light image and a fluorescence image, or a visible-fluorescence mixture image.

(Step S103)

Processing in steps S103 to S106 is image processing in the image processing unit illustrated in FIGS. 2, 3, 5, or the like, for example.

Step S103 executes processing of separating the visible light image and the fluorescence image from each other.

This processing is executed in for example, the image separating unit 301 in FIG. 3 and the image separating unit 321 illustrated in FIG. 5.

In the example illustrated in FIG. 3, the visible-fluorescence mixture image 210 photographed by the imaging unit 106 is input to an image separating unit 301, and then, the visible-fluorescence mixture image 210 is separated into a visible light image 211 constituted with a visible light component similar to an ordinary RGB color image, and a fluorescence image 212 constituted with a fluorescent component alone.

This is executed by matrix operation applying separation matrix, for example.

In the example illustrated in FIG. 5, the visible light image 231 and the fluorescence image 232 sequentially photographed by the imaging unit 106 are input to the image separating unit 321 of the image processing unit 120.

Under the control of the control unit 101, the image separating unit 321 separates an input image from the imaging unit 106 into a visible light image 233 and a fluorescence image 234 by time sharing processing.
(Step S104)

Next, feature amount extraction from the image is performed in step S104.

This processing is processing to be executed by the feature amount classification processing unit illustrated in FIGS. 3 and 5, for example.

The feature amount classification processing unit inputs the visible light image and the fluorescence image, extracts an image feature amount from these images, executes classification processing based on the extracted feature amount and stores data into a storage unit (database), while inputting a feature amount data classification result to the image correction parameter calculation unit.

Note that the feature amount extracted from the image by the feature amount classification processing unit is, for example, a feature amount such as a point spread function (PSF) (=a function indicating a blur mode) being blur mode information.

Note that other feature amounts include, for example, luminance distribution information and noise information, or the like as described above with reference to FIGS. 4A1, 4A2, 4B1, 4B2, 4C1, and 4C2.
(Step S105)

Next, step S105 executes correction parameter calculation processing.

This processing is processing executed by the image correction parameter calculation unit illustrated in FIGS. 3 and 5, for example.

The image correction parameter calculation unit uses the correction mode determination information input from the feature amount classification processing unit and training data stored in the storage unit (database) to determine the image correction parameter to be used for performing image quality enhancement processing on the visible light image and the fluorescence image.

The determined image correction parameter is input to the image correction unit.

Note that one specific example of the correction parameter calculated by the image correction parameter calculation unit is a multiplication coefficient being a setting parameter of an inverse filter for suppressing blur.

The image correction parameter calculation unit generates an inverse filter such as the Wiener filter to be applied for suppressing blur.
(Step S106)

Finally, step S106 executes image correction processing. This processing is processing executed by the image correction unit illustrated in FIGS. 3 and 5, for example.

The image correction unit applies the image correction parameter input from the image correction parameter calculation unit to execute image correction processing on the visible light image and the fluorescence image, and then, generates and outputs the corrected visible light image and the corrected fluorescence image that have undergone image quality enhancement processing.

Note that a specific example of the correction processing is pixel value correction processing that utilizes an inverse filter such as a Wiener filter that executes blur suppression processing.

For example, the blur suppression processing described above with reference to FIGS. 6, 7, 8A, 8B, 8C, 9A, 9B, 9C, and 10 is executed.

The corrected image having blur suppressed and image quality enhanced by this image correction processing is output.

Note that the processing example described with reference to FIGS. 6, 7, 8A, 8B, 8C, 9A, 9B, 9C, and 10 focused on the blur suppression processing on the fluorescence image, while it is also possible to suppress the blur of the visible light image with application of similar processing stages to the visible light image.

[6-2. Image Processing Sequence in a Configuration Executing Time Sharing Photographing of Visible Light Image and Fluorescence Image]

Next, an image processing sequence in a configuration executing time sharing photographing of a visible light image and a fluorescence image will be described with reference to a flowchart illustrated in FIG. 17.

This processing sequence is processing sequence, for example, as illustrated in a configuration in FIGS. 5 and 10 described above, in which the imaging unit 106 alternately photographs a visible light image and a fluorescence image and inputs the images to the image processing unit to execute image processing.

Figure 17:
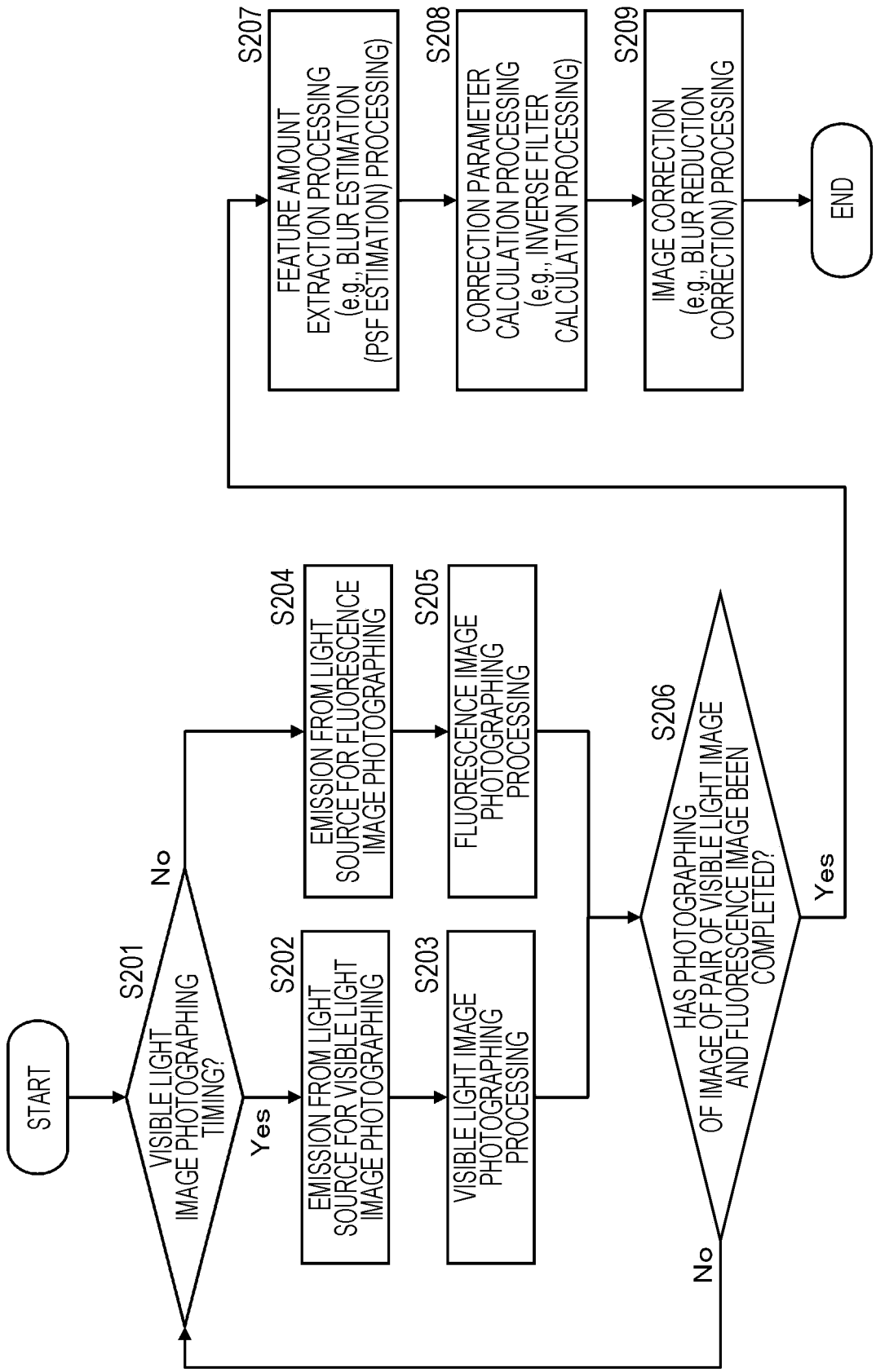
FIG. 17 is a flowchart illustrating a processing sequence executed by an image processing apparatus.

The processing according to the flow illustrated in FIG. 17 is executed under the control of a control unit having a program execution function in accordance with a program stored in the storage unit of the image processing apparatus, for example.

Hereinafter, processing of each of steps of the flow illustrated in FIG. 17 will be sequentially described.
(Step S201)

First, the control unit judges in step S201 whether it is a timing of photographing a visible light image or a timing of photographing a fluorescence image.

In a case where determination is the photographing timing of the visible light image, the processing proceeds to step S202.

In contrast, in a case where determination is the photographing timing of the fluorescence image, the processing proceeds to step S204.
(Steps S202 to S203)

In a case where the control unit determined in step S201 that it is the timing of photographing the visible light image, the imaging unit performs in steps S202 to S203 light emission processing necessary for visible light image photographing and visible light image photographing processing under the control of the control unit.
(Steps S204 to S205)

In contrast, in a case where the control unit determined in step S201 that it is the timing of photographing the fluorescence image, the imaging unit performs in steps S204 to S205 light emission processing necessary for fluorescence image photographing and fluorescence image photographing processing under the control of the control unit.
(Step S206)

Next, the control unit determines in step S206 whether or not photographing of an image pair of a visible light image and a fluorescence image has been completed.

In a case where photographing of the image pair of the visible light image and the fluorescence image has not been completed, the processing returns to step S201, and the processing of step S201 and the subsequent steps is repeated.

In contrast, in a case where photographing of the image pair of the visible light image and the fluorescence image has been completed, the processing proceeds to step S207.

(Step S207)

Processing in steps S207 to S209 is image processing to be executed in the image processing unit illustrated in FIGS. 5, 10, or the like, for example.

In step S207, feature amount extraction from the image is performed.

This processing is processing to be executed by the feature amount classification processing unit illustrated in FIG. 5, for example.

The feature amount classification processing unit inputs the visible light image and the fluorescence image, extracts an image feature amount from these images, executes classification processing based on the extracted feature amount and stores data into a storage unit (database), while inputting a feature amount data classification result to the image correction parameter calculation unit.

Note that the feature amount extracted from the image by the feature amount classification processing unit is, for example, a feature amount such as a point spread function (PSF) (=a function indicating a blur mode) being blur mode information.

Note that other feature amounts include, for example, luminance distribution information and noise information, or the like as described above with reference to FIGS. 4A1, 4A2, 4B1, 4B2, 4C1, and 4C2.

(Step S208)

Next, step S208 executes correction parameter calculation processing.

This processing is processing executed by the image correction parameter calculation unit illustrated in FIG. 5, for example.

The image correction parameter calculation unit uses the correction mode determination information input from the feature amount classification processing unit and training data stored in the storage unit (database) to determine the image correction parameter to be used for performing image quality enhancement processing on the visible light image and the fluorescence image.

The determined image correction parameter is input to the image correction unit.

Note that one specific example of the correction parameter calculated by the image correction parameter calculation unit is a multiplication coefficient being a setting parameter of an inverse filter for suppressing blur.

The image correction parameter calculation unit generates an inverse filter such as the Wiener filter to be applied for suppressing blur.

(Step S209)

Finally, step S209 executes image correction processing.

This processing is, for example, processing executed by the image correction unit illustrated in FIG. 5.

The image correction unit applies the image correction parameter input from the image correction parameter calculation unit to execute image correction processing on the visible light image and the fluorescence image, and then, generates and outputs the corrected visible light image and the corrected fluorescence image that have undergone image quality enhancement processing.

Note that a specific example of the correction processing is pixel value correction processing that utilizes an inverse filter such as a Wiener filter that executes blur suppression processing.

For example, the blur suppression processing described above with reference to FIGS. 6, 7, 8A, 8B, 8C, 9A, 9B, 9C, and 10 is executed.

The corrected image having blur suppressed and image quality enhanced by this image correction processing is output.

Note that the processing example described with reference to FIGS. 6, 7, 8A, 8B, 8C, 9A, 9B, 9C, and 10 focused on the blur suppression processing on the fluorescence image, while it is also possible to suppress the blur of the visible light image with application of similar processing stages to the visible light image.

[6-3. Image processing sequence in a configuration of consecutively photographing images according to mode by setting image photographing modes of visible light images and fluorescence images]

Next, an image processing sequence in a configuration of performing consecutive photographing of an image according to modes by setting each of image photographing modes of the visible light image and the fluorescence image will be described with reference to a flowchart illustrated in FIG. 18.

This processing sequence is, for example, a processing sequence in the case of executing the image photographing processing described above with reference to FIGS. 15A and 15B.

Figure 18:
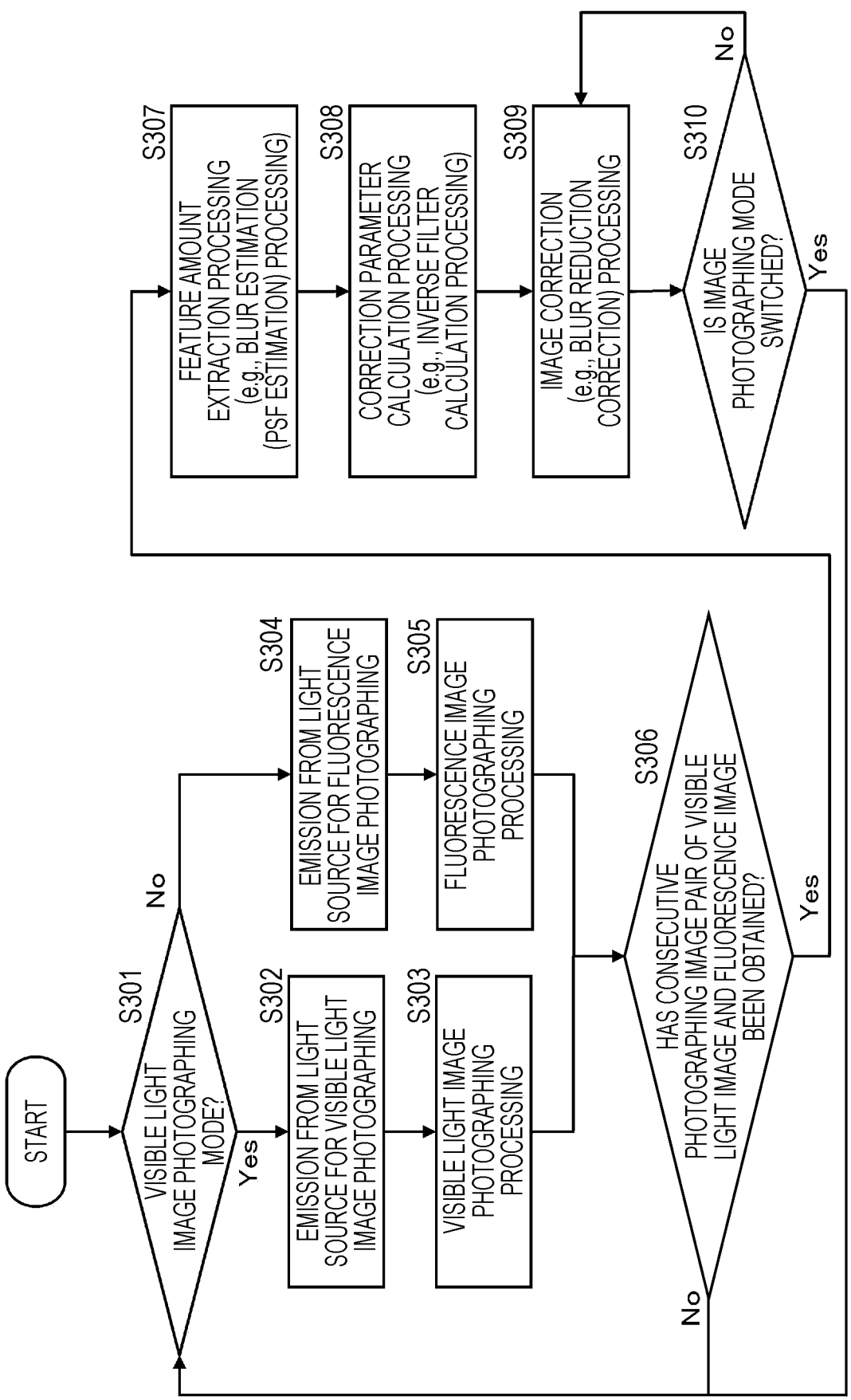
FIG. 18 is a flowchart illustrating a processing sequence executed by an image processing apparatus.

In other words, the flow illustrated in FIG. 18 is a flow illustrating processing in a case where the setting enables a visible light image photographing mode that executes consecutive photographing of a visible light image and a fluorescence image photographing mode that executes consecutive photographing of a fluorescence image to be alternately switched, as illustrated in the image sequence of photographed images in FIG. 15A.

The processing according to the flow illustrated in FIG. 18 is executed under the control of the control unit having a program execution function in accordance with a program stored in the storage unit of the image processing apparatus, for example.

Hereinafter, processing of each of steps of the flow illustrated in FIG. 18 will be sequentially described.

(Step S301)

First, in step S301, the control unit judges whether the current photographing mode is the visible light image photographing mode that executes consecutive photographing of a visible light image or the fluorescence image photographing mode that executes consecutive photographing of a fluorescence image.

In a case where determination is the visible light image photographing mode, the processing proceeds to step S302.

In contrast, in a case where determination is the fluorescence image photographing mode, the processing proceeds to step S304.

(Steps S302 to S303)

In a case where the control unit determined in step S301 that it is the visible light image photographing mode, the imaging unit performed in steps S302 to S303 light emission processing necessary for visible light image photographing and visible light image photographing processing under the control of the control unit.

(Steps S304 to S305)

In contrast, in a case where the control unit determined in step S301 that it is the fluorescence image photographing mode, the imaging unit performs in steps S304 to S305 light emission processing necessary for fluorescence image photographing and fluorescence image photographing processing under the control of the control unit.
(Step S306)

Next, in step S306, the control unit determines whether or not a consecutive photographed image pair of a visible light image and a fluorescence image has been obtained.

The timing of determination that the consecutive photographed image pair of the visible light image and the fluorescence image has been obtained is a timing of acquisition of the fluorescence image (f4) illustrated in FIGS. 15A and 15B, for example.

In a case where it is not a timing of obtaining a consecutive photographed image pair of the visible light image and the fluorescence image, the processing returns to step S301, and the processing of step S301 and the subsequent steps is repeated.

In contrast, in a case where it is determined that the consecutive photographed image pair of the visible light image and the fluorescence image has been obtained, the processing proceeds to step S307.
(Step S307)

Processing in steps S307 to S309 is image processing to be executed in the image processing unit illustrated in FIGS. 2, 3, 5, or the like, for example.

In step S307, feature amount extraction from the image is performed.

This processing is processing to be executed by the feature amount classification processing unit illustrated in FIGS. 3, 5, or the like, for example.

The feature amount classification processing unit inputs the visible light image and the fluorescence image, extracts an image feature amount from these images, executes classification processing based on the extracted feature amount and stores data into a storage unit (database), while inputting a feature amount data classification result to the image correction parameter calculation unit.

Note that the feature amount extracted from the image by the feature amount classification processing unit is, for example, a feature amount such as a point spread function (PSF) (=a function indicating a blur mode) being blur mode information.

Note that other feature amounts include, for example, luminance distribution information and noise information, or the like as described above with reference to FIGS. 4A1, 4A2, 4B1, 4B2, 4C1, and 4C2.
(Step S308)

Next, step S308 executes correction parameter calculation processing.

This processing is processing executed by the image correction parameter calculation unit illustrated in FIGS. 3, 5, or the like, for example.

The image correction parameter calculation unit uses the correction mode determination information input from the feature amount classification processing unit and training data stored in the storage unit (database) to determine the image correction parameter to be used for performing image quality enhancement processing on the visible light image and the fluorescence image.

The determined image correction parameter is input to the image correction unit.

Note that one specific example of the correction parameter calculated by the image correction parameter calculation unit is a multiplication coefficient being a setting parameter of an inverse filter for suppressing blur.

The image correction parameter calculation unit generates an inverse filter such as the Wiener filter to be applied for suppressing blur.
(Step S309)

Finally, step S309 executes image correction processing. This processing is processing executed by the image correction unit illustrated in FIGS. 3, 5, or the like, for example.

The image correction unit applies the image correction parameter input from the image correction parameter calculation unit to execute image correction processing on the visible light image and the fluorescence image, and then, generates and outputs the corrected visible light image and the corrected fluorescence image that have undergone image quality enhancement processing.

Note that a specific example of the correction processing is pixel value correction processing that utilizes an inverse filter such as a Wiener filter that executes blur suppression processing.

For example, the blur suppression processing described above with reference to FIGS. 6, 7, 8A, 8B, 8C, 9A, 9B, 9C, and 10 is executed.

The corrected image having blur suppressed and image quality enhanced by this image correction processing is output.

Note that the processing example described with reference to FIGS. 6, 7, 8A, 8B, 8C, 9A, 9B, 9C, and 10 focused on the blur suppression processing on the fluorescence image, while it is also possible to suppress the blur of the visible light image with application of similar processing stages to the visible light image.
(Step S310)

Next, step S310 determines whether or not switching of the image photographing mode has occurred.

In a case where it is determined that switching of the image photographing mode has not occurred, that is, same type of image photographing is continuously performed, the processing returns to step S309 and image correction is performed on the image. This image correction is executed using the correction mode and the correction parameter determined on the basis of the consecutive photographed image pair of the visible light image and the fluorescence image obtained in step S306.

This processing corresponds to image correction processing for the fluorescence image (f5) to the fluorescence image (f7) illustrated in FIGS. 15A and 15B, for example.

Image correction on the fluorescence image (f5) to the fluorescence image (f7) illustrated in FIGS. 15A and 15B is executed using the correction mode and the correction parameter determined on the basis of the visible light image (f3) and the fluorescence image (f4).

In a case where it is determined in step S310 that switching of the image photographing mode has occurred, the processing returns to step S301, and processing of step S301 and the subsequent steps are executed.

With the processing according to this flow, image correction can be performed on all images even in a case where the image photographing sequence as illustrated in FIGS. 15A and 15B described above has been executed.

[7. Hardware Configuration Example of Image Processing Apparatus]

Next, an example of the hardware configuration of the image processing apparatus will be described with reference to FIG. 19.

Figure 19:
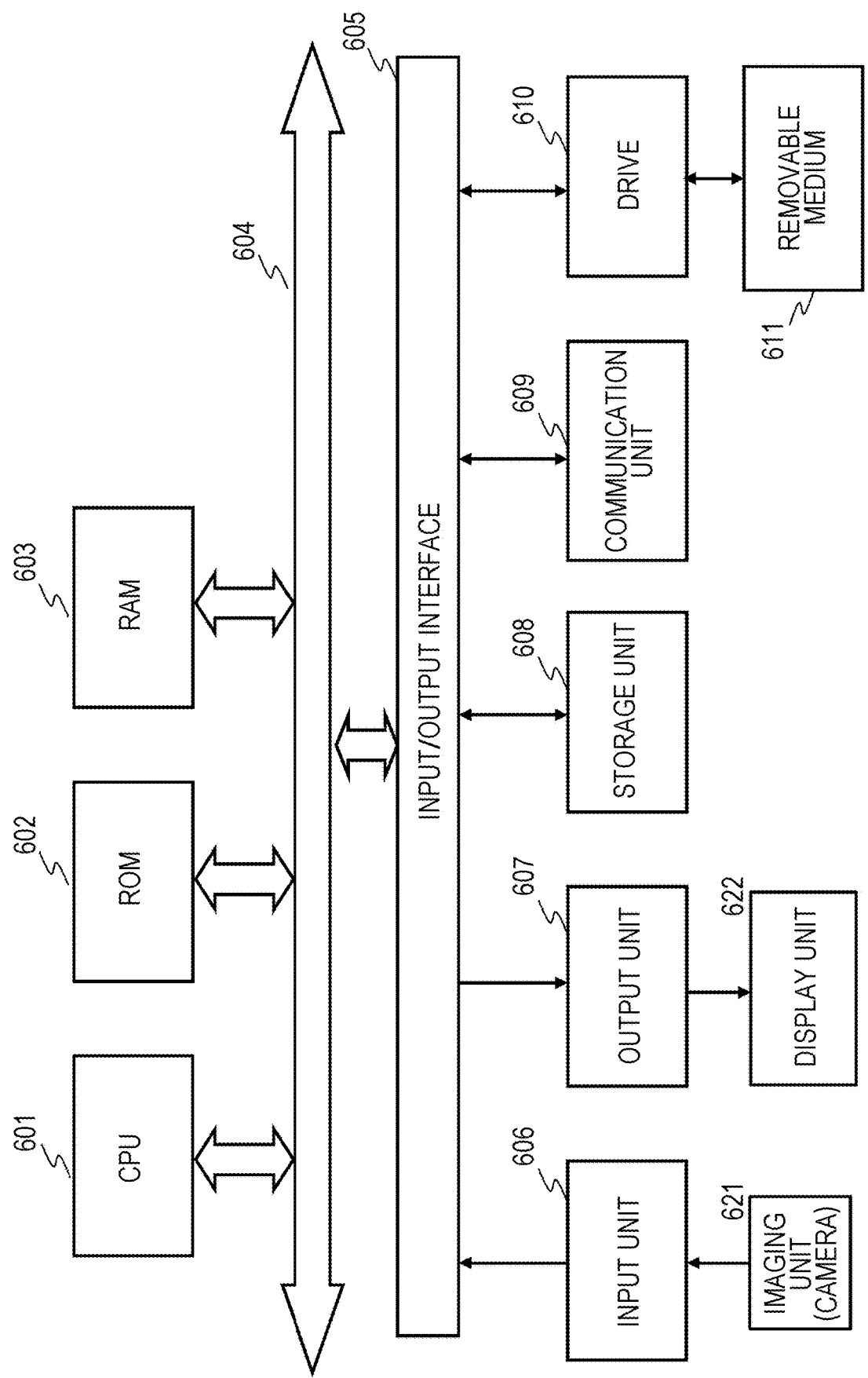
FIG. 19 is a diagram illustrating an example of a hardware configuration of an image processing apparatus.

FIG. 19 is a diagram illustrating a hardware configuration example of an image processing apparatus that executes processing of the present disclosure.

A central processing unit (CPU) 601 functions as a control unit or a data processing unit that executes various types of processing in accordance with a program stored in a read only memory (ROM) 602 or a storage unit 608. For example, the processing according to the sequence described in the above exemplary embodiment is executed. A random access memory (RAM) 603 stores programs executed by the CPU 601, data, or the like. The CPU 601, the ROM 602, and the RAM 603 are mutually connected by a bus 604.

The CPU 601 is connected to an input/output interface 605 via the bus 604. The input/output interface 605 is connected to an input unit 606 that inputs a photographed image of an imaging unit 621, and including various switches, a keyboard, a mouse, a microphone, or the like that can be used for user input, and also connected to an output unit 607 that executes data output to a display unit 622, a speaker, or the like. The CPU 601 executes various types of processing in accordance with an instruction input from the input unit 606, and outputs processing results to the output unit 607, for example.

The storage unit 608 connected to the input/output interface 605 includes a hard disk or the like, for example, and stores a program to be executed by the CPU 601 and various data. A communication unit 609 functions as a transmission/reception unit for Wi-Fi communication, Bluetooth (registered trademark) communication, and other data communication via a network such as the Internet, a local area network, or the like, and communicates with an external apparatus.

A drive 610 connected to the input/output interface 605 drives a removable medium 611 such as a magnetic disk, an optical disk, a magneto-optical disk or a semiconductor memory such as a memory card or the like, and executes data recording or reading.

[8. Summary of Configuration Of Present Disclosure]

The exemplary embodiments of the present disclosure have been described in detail with reference to specific exemplary embodiments as above. Still, it is self-evident that those skilled in the art can make modifications and substitutions of the exemplary embodiments without departing from the scope and spirit of the present disclosure. In other words, the present invention has been disclosed in the form of exemplification, and should not be interpreted restrictively. In order to judge the scope of the present disclosure, the section of claims should be taken into consideration.

Note that the technology disclosed in the present description can be configured as follows.

(1) An image processing apparatus including:
a feature amount classification processing unit that inputs a fluorescence image and a visible light image and extracts a feature amount from at least one of the images; and
an image correction unit that executes pixel value correction processing on the fluorescence image on the basis of a correction parameter determined in accordance with the feature amount.

(2) The image processing apparatus according to (1), further including a correction parameter calculation unit that determines a correction parameter to be used for pixel value correction in the image correction unit on the basis of the feature amount,
in which the image correction unit
executes pixel value correction processing applying a correction parameter determined by the correction parameter calculation unit.

(3) The image processing apparatus according to (1) or (2),
in which the feature amount classification processing unit obtains blur mode information from the fluorescence image, and
the image correction unit
executes pixel value correction processing on the fluorescence image so as to reduce blur of the fluorescence image.

(4) The image processing apparatus according to (3), further including a correction parameter calculation unit that determines a correction parameter to be used for pixel value correction in the image correction unit on the basis of the feature amount,
in which the correction parameter calculation unit determines a correction parameter to suppress blur of the fluorescence image, and
the image correction unit
executes pixel value correction processing applying a correction parameter determined by the correction parameter calculation unit.

(5) The image processing apparatus according to any of (1) to (4), in which the feature amount classification processing unit extracts one feature amount out of (a) to (c):
(a) luminance distribution information;
(b) blur mode information; and
(c) noise information,
from at least one of the fluorescence image or the visible light image.

(6) The image processing apparatus according to any of (1) to (5), further including an image separating unit that inputs a mixed image of a visible light image and a fluorescence image and generates a visible light image and a fluorescence image from the mixed image,
in which the feature amount classification processing unit inputs the fluorescence image and the visible light image generated by the image separating unit, and
the image correction unit
executes pixel value correction processing based on a correction parameter determined in accordance with the feature amount, onto the fluorescence image generated by the image separating unit.

(7) The image processing apparatus according to any of (1) to (6),
further including
an image separating unit that alternately inputs a visible light image and a fluorescence image, separates an input image into a visible light image and a fluorescence image and outputs the images,
in which the feature amount classification processing unit inputs the fluorescence image and the visible light image output by the image separating unit, and
the image correction unit
executes pixel value correction processing based on a correction parameter determined in accordance with the feature amount, onto the fluorescence image output by the image separating unit.

(8) The image processing apparatus according to any of (1) to (7),
in which, in a case where fluorescence images are consecutive as the input image,
the image correction unit
applies a correction parameter determined on the basis of a feature amount obtained by application of a consecutive photographed image pair of a visible light image and a fluorescence image that are closest in time in the past so as to execute correction processing of the consecutively input fluorescence images.

(9) The image processing apparatus according to any of (1) to (8), further including an interpolation image generation unit that generates a virtual fluorescence image at non-photographing timing of fluorescence images on the basis of preceding and succeeding photographed images, in which the feature amount classification processing unit inputs the interpolation image generated by the interpolation image generation unit to execute feature amount extraction processing, and the image correction unit executes pixel value correction processing based on a correction parameter determined in accordance with the feature amount, onto the interpolation image generated by the interpolation image generation unit.

(10) The image processing apparatus according to any of (1) to (9), in which the image correction unit executes pixel value correction processing on the visible light image on the basis of a correction parameter determined in accordance with the feature amount.

(11) An imaging apparatus including:

an imaging unit that performs imaging processing of a visible light image and a fluorescence image, or a visible-fluorescence mixture image;

an image separating unit that inputs a photographed image of the imaging unit, separates a visible light image and a fluorescence image from the input image and outputs the separated images;

a feature amount classification processing unit that inputs the fluorescence image and the visible light image output by the image separating unit and extracts a feature amount from at least one of the images; and an image correction unit that executes pixel value correction processing on the fluorescence image output by the image separating unit on the basis of a correction parameter determined in accordance with the feature amount.

(12) The imaging apparatus according to (11), further including a correction parameter calculation unit that determines a correction parameter to be used for pixel value correction in the image correction unit on the basis of the feature amount, in which the image correction unit executes pixel value correction processing applying a correction parameter determined by the correction parameter calculation unit.

(13) The imaging apparatus according to (11) or (12) claim 11, in which the feature amount classification processing unit obtains blur mode information from the fluorescence image, and the image correction unit executes pixel value correction processing on the fluorescence image so as to reduce blur of the fluorescence image.

(14) The imaging apparatus according to (13), further including a correction parameter calculation unit that determines a correction parameter to be used for pixel value correction in the image correction unit on the basis of the feature amount, in which the correction parameter calculation unit determines a correction parameter to suppress blur of the fluorescence image, and the image correction unit executes pixel value correction processing applying a correction parameter determined by the correction parameter calculation unit.

(15) An image processing method executed in an image processing apparatus, the image processing method including executing:

a feature amount calculation step of executing, by a feature amount classification processing unit, input of a fluorescence image and a visible light image and extraction of a feature amount from at least one of the images; and an image correction step of executing, by an image correction unit, pixel value correction processing on the fluorescence image on the basis of a correction parameter determined in accordance with the feature amount.

(16) A program that causes an image processing apparatus to execute image processing, the image processing including processing of:

causing a feature amount classification processing unit to input a fluorescence image and a visible light image and extract a feature amount from at least one of the images; and causing an image correction unit to execute pixel value correction processing on the fluorescence image on the basis of a correction parameter determined in accordance with the feature amount.

Furthermore, the series of processing described in the description can be executed by hardware, software, or a combination of both. In the case of executing the processing by software, it is possible to allow the program recording processing sequences to be installed and executed on a memory within a computer, incorporated in dedicated hardware, or possible to allow the program to be installed and executed on a general-purpose computer capable of executing various types of processing. For example, the program can be recorded in a recording medium beforehand. The program can be installed from a recording medium to a computer, or can be received via a network such as a local area network (LAN) or the Internet so as to be installed in a recording medium such as a built-in hard disk.

Note that the various types of processing described in the description may be executed in parallel or separately in accordance with the processing capability of the apparatus that executes the processing or in accordance with necessity, in addition to execution in time series following the description. Note that in the present description, the system represents a logical set of a plurality of apparatuses, and that all the constituent apparatuses need not be in a same housing.

INDUSTRIAL APPLICABILITY

As described above, according to a configuration of one exemplary embodiment of the present disclosure, it is possible to implement an apparatus and a method to execute image quality enhancement processing on fluorescence images.

Specifically, the fluorescence image and the visible light image are input and the image feature amount is extracted, and pixel value correction processing is executed on the fluorescence image on the basis of a correction parameter determined in accordance with the feature amount. The correction parameter used for pixel value correction is determined by the correction parameter calculation unit on the basis of the feature amount. The image correction unit executes pixel value correction processing that applies the correction parameter determined by the correction parameter calculation unit. For example, blur mode information is obtained as a feature amount from a fluorescence image, and the image correction unit executes pixel value correction processing on the fluorescence image so as to reduce blur of the fluorescence image.

This processing enables implementation of an apparatus and a method for executing image quality enhancement processing on a fluorescence image.

REFERENCE SIGNS LIST

10 Living tissue
11 Blood vessel
100 Image processing apparatus
101 Control unit
102 Storage unit
103 Codec
104 Input unit
105 Output unit
106 Imaging unit
151 Corrected visible light image
152 Corrected fluorescence image
301 Image separating unit
302 Feature amount classification processing unit
303 Storage unit (database)
304 Image correction parameter calculation unit
305 Image correction unit
321 Image separating unit
322 Feature amount classification processing unit
333 Storage unit (database)
324 Image correction parameter calculation unit
325 Image correction unit
330 PSF estimation unit
340 Inverse filter calculation unit
350 PSF estimation unit
360 Inverse filter calculation unit
400 Image processing apparatus
410 Interpolation image generation unit
411 Motion estimation processing (ME) unit
412 Interpolation image estimation unit
413 Subtraction unit
450 Image processing unit
451 Feature amount classification processing unit
452 Storage unit (database)
453 Image correction parameter calculation unit
454 Image correction unit
501 Image feature amount classification processing unit
502 Image correction parameter calculation unit
503 Image correction unit
601 CPU
602 ROM
603 RAM
604 Bus
605 Input/output interface
606 Input unit
607 Output unit
608 Storage unit
609 Communication unit
610 Drive
611 Removable medium
621 Imaging unit
622 Display unit

The invention claimed is:

1. An image processing apparatus, comprising:
a memory configured to store training data; and
a central processing unit (CPU) configured to:
input a visible-fluorescence mixture image;
separate, based on a separation matrix, the visible-fluorescence mixture image into a first visible light image and a first fluorescence image;
extract a first feature amount from at least one of the first fluorescence image or the first visible light image;
determine a specific correction mode based on the extracted first feature amount and the stored training data;
determine a first correction parameter based on the determined specific correction mode; and
execute pixel value correction processing on the first fluorescence image based on the determined first correction parameter.

2. The image processing apparatus according to claim 1, wherein
the extracted first feature amount includes blur mode information, and
the executed pixel value correction processing corresponds to reduction of a blur of the first fluorescence image.

3. The image processing apparatus according to claim 2, wherein
the reduction of the blur of the first fluorescence image is based on the determined first correction parameter, and
the determined first correction parameter is based on the blur mode information.

4. The image processing apparatus according to claim 1, wherein the extracted first feature amount includes at least one of luminance distribution information, blur mode information, or noise information.

5. The image processing apparatus according to claim 1, wherein the CPU is further configured to:
input images corresponding to a second visible light image and a second fluorescence image;
separate the input images into the second visible light image and the second fluorescence image;
extract a second feature amount from at least one of the second fluorescence image or the second visible light image;
determine a second correction parameter based on the extracted second feature amount; and
execute the pixel value correction processing on the second fluorescence image based on the determined second correction parameter.

6. The image processing apparatus according to claim 1, wherein the CPU is further configured to:
input consecutive fluorescence images;
obtain a second feature amount based on a consecutive photographed image pair of a second visible light image and a second fluorescence image;
determine a second correction parameter based on the second feature amount; and
execute correction processing of the consecutive fluorescence images based on the second correction parameter.

7. The image processing apparatus according to claim 1, wherein the CPU is further configured to:
generate a virtual fluorescence image at a non-photographing timing of fluorescence images, based on a preceding photographed image and a succeeding photographed image;
extract a second feature amount from the generated virtual fluorescence image; and
determine the first correction parameter based on the extracted second feature amount.

8. The image processing apparatus according to claim 1, wherein the CPU is further configured to execute the pixel value correction processing on the first visible light image based on the determined first correction parameter.

9. An imaging apparatus, comprising:
a memory configured to store training data;
an imager configured to photograph a visible-fluorescence mixture image; and
a central processing unit (CPU) configured to:
- input the photographed visible-fluorescence mixture image;
- separate, based on a separation matrix, the photographed visible-fluorescence mixture image into a visible light image and a fluorescence image;
- extract a feature amount from at least one of the fluorescence image or the visible light image;
- determine a specific correction mode based on the extracted feature amount and the stored training data;
- determine a correction parameter based on the determined specific correction mode; and
- execute pixel value correction processing on the fluorescence image based on the determined correction parameter.

10. The imaging apparatus according to claim 9, wherein
the extracted feature amount includes blur mode information, and
the executed pixel value correction processing corresponds to reduction of a blur of the fluorescence image.

11. The imaging apparatus according to claim 10, wherein
the reduction of the blur of the fluorescence image is based on the determined correction parameter, and
the determined correction parameter is based on the blur mode information.

12. An image processing method, comprising:
in an image processing apparatus that includes a memory:
- storing training data in the memory;
- inputting a visible-fluorescence mixture image;
- separating, based on a separation matrix, the visible-fluorescence mixture image into a visible light image and a fluorescence image;
- extracting a feature amount from at least one of the fluorescence image or the visible light image;
- determining a specific correction mode based on the extracted feature amount and the stored training data;
- determining a correction parameter based on the determined specific correction mode; and
- executing pixel value correction processing on the fluorescence image based on the determined correction parameter.

13. A non-transitory computer-readable medium having stored thereon computer-executable instructions which, when executed by an image processing apparatus, cause the image processing apparatus to execute operations, the operations comprising:
- storing training data in a memory of the image processing apparatus;
- inputting a visible-fluorescence mixture image;
- separating, based on a separation matrix, the visible-fluorescence mixture image into a visible light image and a fluorescence image;
- extracting a feature amount from at least one of the fluorescence image or the visible light image;
- determining a specific correction mode based on the extracted feature amount and the stored training data;
- determining a correction parameter based on the determined specific correction mode; and
- executing pixel value correction processing on the fluorescence image based on the determined correction parameter.

* * * * *